(12) United States Patent
Merenov et al.

(10) Patent No.: US 8,901,346 B2
(45) Date of Patent: *Dec. 2, 2014

(54) APPARATUS, SYSTEMS, AND METHODS FOR PURIFICATION OF ISOCYANATE MIXTURES

(75) Inventors: Andrei S. Merenov, Lake Jackson, TX (US); Luca Balbo, Lake Jackson, TX (US); Douglas A. Stallard, Lake Jackson, TX (US); John G. Pendergrast, Jr., Lake Jackson, TX (US); Joerg-Peter Gehrke, Stade (DE); Amilcar R. Collado, Clute, TX (US); David D. Hibbitts, Charlottesville, VA (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/063,817

(22) PCT Filed: Oct. 1, 2009

(86) PCT No.: PCT/US2009/059241
§ 371 (c)(1),
(2), (4) Date: Mar. 14, 2011

(87) PCT Pub. No.: WO2010/039965
PCT Pub. Date: Apr. 8, 2010

(65) Prior Publication Data
US 2011/0178328 A1    Jul. 21, 2011

Related U.S. Application Data

(60) Provisional application No. 61/102,128, filed on Oct. 2, 2008, provisional application No. 61/102,141, filed on Oct. 2, 2008.

(51) Int. Cl.
*C07C 263/20* (2006.01)
*B01D 3/14* (2006.01)

(52) U.S. Cl.
CPC .............. *C07C 263/20* (2013.01); *B01D 3/141* (2013.01); *B01D 3/14* (2013.01)
USPC .......................................... 560/352; 560/330

(58) Field of Classification Search
USPC ............................ 560/330, 352; 422/608, 600
See application file for complete search history.

(56) References Cited

U.S. PATENT DOCUMENTS

| | | | |
|---|---|---|---|
| 3,449,216 A | 6/1969 | Baird | B01D 3/10 |
| 3,536,610 A | 10/1970 | Stork | 208/340 |
| 4,566,947 A | 1/1986 | Tsuruta | 203/26 |
| 4,824,527 A | 4/1989 | Erickson | 203/25 |
| 5,346,593 A | 9/1994 | Cialkowski et al. | 203/18 |
| 7,118,653 B2 * | 10/2006 | Brady et al. | 203/29 |
| 8,124,035 B2 * | 2/2012 | Riley | 422/630 |
| 8,158,086 B2 * | 4/2012 | Terada et al. | 422/600 |
| 2003/0230476 A1 | 12/2003 | Brady et al. | |
| 2003/0233013 A1 | 12/2003 | Lokum et al. | 560/352 |
| 2005/0211541 A1 | 9/2005 | Bassler et al. | 203/29 |
| 2006/0137967 A1 | 6/2006 | Kister et al. | 203/2 |
| 2006/0173206 A1 | 8/2006 | Schal et al. | 558/419 |
| 2007/0015934 A1 | 1/2007 | Wolfert et al. | 560/347 |
| 2009/0139852 A1 | 6/2009 | VanNuland et al. | 203/49 |
| 2010/0193348 A1 | 8/2010 | Heydrich et al. | 203/71 |

FOREIGN PATENT DOCUMENTS

| | | | |
|---|---|---|---|
| EP | 1 371 634 | 12/2003 | ............ C07C 263/20 |
| EP | 1 371 635 | 12/2003 | ............ C07C 263/20 |
| JP | 2004-155760 | 6/2004 | ............ C07C 263/20 |

OTHER PUBLICATIONS

International Search Report with Written Opinion in International Application No. PCT/US2009/059241, dated Apr. 6, 2010, 16 pages, Mailing Date Apr. 6, 2010.
Schultz et al., "Reduce Costs with Dividing-Wall Columns", Chemical Engineering Progress, American Institute of Chemical Engineers, vol. 98, No. 5, pp. 64-71, May 1, 2002.
International Preliminary Report on Patentability and Written Opinion; PCT2009/059241; pp. 9, Apr. 14, 2011.
International Preliminary Report on Patentability and Written Opinion; PCT2009/059249; pp. 9, Apr. 14, 2011.
Japanese Office Action English Translation; Application No. 2011-530237; pp. 4, Apr. 30, 2013.
English Translation of the First Office Action of the Chinese Patent Office; Application No. 200980146951.7; Pgs, Jan. 18, 2013.
Kaibo Zhang et al.; "Preparation of Phenyl Isocyanates"; Agrochemicals, vol. 32, No. 4; pp. 9-10; http://www.cnki.net, Dec. 31, 1993.
International Search Report with Written Opinion in International Application No. PCT/US2009/059249, dated May 12, 2010, 16 pages, May 12, 2010.
Chinese Office Action, with English Translation, Application No. 200980146954.0; 4 pages, Mar. 22, 2013.

* cited by examiner

*Primary Examiner* — Sudhakar Katakam
*Assistant Examiner* — Pancham Bakshi
(74) *Attorney, Agent, or Firm* — Baker Botts L.L.P.

(57) ABSTRACT

The present disclosure relates, according to some embodiments, to apparatus, systems, and/or methods for fractionating a feed mixture comprising, for example, one or more isocyanates, light components, solvents and/or heavier components. In some embodiments, fractionating an isocyanate feed mixture may comprise distilling the feed mixture in a non-adiabatic fractionating apparatus comprising a prefractionating section and/or column and a main section and/or column, which comprises a rectification section, a side section, and a stripping section. For example, isocyanates may be separated from light component(s), solvent(s) and/or heavier component(s). A fractionating apparatus may be configured and arranged, in some embodiments, as a dividing wall column. According to some embodiments of the disclosure, apparatus, systems, and/or methods may be energy efficient and/or may have a broad operating range.

16 Claims, 9 Drawing Sheets

APPARATUS, SYSTEMS, AND METHODS FOR PURIFICATION OF ISOCYANATE MIXTURES

RELATED APPLICATIONS

This application is a 371 U.S. national application of International Application Number PCT/US2009/059241 filed Oct. 1, 2009, which designates the U.S.; and claims the benefit of U.S. Provisional Patent Application Ser. No. 61/102,128 filed Oct. 2, 2008, and U.S. Provisional Patent Application Ser. No. 61/102,141 filed Oct. 2, 2008, which are incorporated by reference in their entirety.

FIELD OF THE DISCLOSURE

The present disclosure relates, in some embodiments, to fractionation of compositions comprising two or more components. For example, the present disclosure relates to distillation of isocyanate mixtures.

BACKGROUND OF THE DISCLOSURE

Polyurethane-based foam may be used in a wide variety of products including, for example, automotive crash pads, sound insulation, vibration dampening, carpet backing, bedding, upholstery, furniture, and packing materials. Polyurethanes may be formed by reacting an isocyanate with a polyol. Isocyanates, in turn, may be formed by various methods. For example, isocyanates may be formed by reacting an amine (e.g., amine, amine hydrochloride, carbamate salt, and/or urea) with phosgene either in a liquid phase in the presence of a solvent or in a vapor phase with solvent added during a quench/cooling stage. Phosgene may be removed from this product mixture to form an isocyanate-containing feed for subsequent distillation.

Distillation columns may be used to fractionate a feed mixture into some or all of its component parts. For example, a distillation column may be used to separate a two-component feed mixture into two product streams: an upper product stream from the top of the column containing the lighter stream and a lower product stream from the bottom of the column containing the heavier component. A distillation column may be configured to yield a side product stream to separate, for example, more complex feed mixtures. However, this side product stream may be contaminated with light or heavy components depending on its location on the column. For example, a side product stream may be contaminated by lateral mixing of the components within the column and/or volatiles passing the side outlet on their way to the top of the column.

Lateral mixing may be reduced or eliminated in a distillation column with a vertical partition that divides the column into separate feed and outlet sections. Problems with contamination may persist, for example, where a feed mixture contains higher levels of lighter components. Reducing this contamination may require additional columns and/or additional thermal input, which may undesirably increase capital and/or production costs.

SUMMARY

Accordingly, a need has arisen for improved distillation apparatus, systems, and methods.

The present disclosure relates, according to some embodiments, to apparatus, systems, and/or methods for fractionating a feed mixture comprising two or more components. A feed mixture may comprise, for example, one or more isocyanates, light components, solvents and/or heavier components. In some embodiments, fractionating a feed mixture (e.g., an isocyanate feed mixture) may comprise distilling the feed mixture in a non-adiabatic fractionating apparatus comprising a prefractionating section and/or column and a main section and/or column, wherein the main section and/or column comprises a rectification section, a side section, and a stripping section. For example, isocyanates may be separated from light component(s), solvent(s) and/or heavier component(s). In some embodiments, fractionating a feed mixture may comprise heating the lower stream of the prefractionating section in an intermediate reboiler. A fractionating apparatus may be configured and arranged, in some embodiments, as a dividing wall column. According to some embodiments of the disclosure, apparatus, systems, and/or methods may be energy efficient and/or may have a broad operating range.

The present disclosure relates, in some embodiments, to a non-adiabatic fractionating apparatus for fractionating an isocyanate mixture. A non-adiabatic fractionating apparatus may comprise, for example, a dividing wall column comprising (a) a prefractionating section comprising an upper and lower end and at least one intermediate reboiler and (b) a main section. In some embodiments, a main section may comprise (i) a rectification section in fluid communication with the upper end of the prefractionating section, (ii) a condenser in fluid communication with the rectification section, (iii) a stripping section in fluid communication with the lower end of the prefractionating section, (iv) a stripping section reboiler in fluid communication with the stripping section, and/or (v) a side section in fluid communication with the rectification section and the stripping section. A non-adiabatic fractionating apparatus may comprise, for example, (a) a prefractionating column comprising an upper and lower end and at least one intermediate reboiler and (b) a main column. In some embodiments, a main column may comprise (i) a rectification section in fluid communication with the upper end of the prefractionating column, (ii) a condenser in fluid communication with the rectification section, (iii) a stripping section in fluid communication with the lower end of the prefractionating column, (iv) a stripping section reboiler in fluid communication with the stripping section, and/or (v) a side section in fluid communication with the rectification section and the stripping section. A non-adiabatic fractionating apparatus may be configured and arranged to have a liquid recycle ratio of from about 0.01 to about 0.5 and/or a vapor recycle ratio of from about 0 to about 0.75 according to some embodiments. An intermediate reboiler, in some embodiments, may be configured and arranged as an internal heat transfer device and/or an external reboiler. According to some embodiments, a non-adiabatic fractionating apparatus may further comprise a pump configured and arranged to pressurize an internal stream. A distillation column may be configured and arranged to consume from about 0.05 to about 0.4 kilowatts per kilogram of isocyanate produced and/or from about 0.4 to about 1.0 kilowatts per kilogram of isocyanate produced in some embodiments. A distillation column may be configured and arranged to receive a feed comprising less than about 20% isocyanate.

The present disclosure relates, in some embodiments, to a method for fractionating an isocyanate feed mixture comprising a light component, a middle-boiling component, and a heavy boiling component using a fractionating apparatus comprising a prefractionating section, a rectification section, a stripping section, and a side section. A method for fractionating an isocyanate feed mixture may comprise, for example, (a) moving the isocyanate feed mixture into the prefractionating section, (b) warming the contents of the prefractionating section and forming a prefractionating section vapor stream $PS_{VS}$ and a prefractionating section liquid stream $PS_{LS}$, (c) moving at least a portion of the prefractionating section vapor stream $PS_{VS}$ to the rectification section, (d) cooling the contents of the rectification section to form a rectification section vapor product stream $RS_{VPS}$ and a condensate liquid, (e) removing from the fractionating apparatus at least a portion of the rectification section vapor product stream $RS_{VPS}$, (f) removing from the fractionating apparatus at least a portion of the condensate liquid as a rectification section liquid product stream $RS_{LPS}$, (g) removing from the rectification section at least a portion of the condensate liquid as a rectification section liquid stream $RS_{LS}$, (h) moving at least a portion of the rectification section liquid stream $RS_{LS}$ to the side section, (i) moving at least a portion of the rectification section liquid stream $RS_{LS}$ to the prefractionating section, (j) heating at least a portion of the prefractionating section liquid stream $PS_{LS}$ to form a second prefractionating section vapor stream $sPS_{VS}$ and a second prefractionating section liquid stream $sPS_{LS}$ and combining each with their respective first streams, (k) moving at least a portion of the prefractionating section liquid stream $PS_{LS}$ from the prefractionating section to the stripping section, (l) heating the contents of the stripping section to form a stripping section vapor stream $SS_{VS}$ and a stripping section lower product stream $SS_{LPS}$, (m) removing from the fractionating apparatus at least a portion of the stripping section liquid product stream $SS_{LPS}$, (n) moving at least a portion of the stripping section vapor stream $SS_{VS}$ to the side section, (o) commingling at least a portion of the rectification section liquid stream $RS_{LS}$ and at least a portion of the stripping section vapor stream $SS_{VS}$ in the side section under conditions that permit formation of a side section vapor stream $SdS_{VS}$, a side section liquid product stream $SdS_{LPS}$, and a side section liquid stream $SdS_{LS}$, (p) removing from the fractionating apparatus at least a portion of the side section liquid product stream $SdS_{LPS}$, (q) moving at least a portion of the side section vapor stream $SdS_{VS}$ to the rectification section, and (r) moving at least a portion of the side section liquid stream $SdS_{LS}$ to the stripping section. In some embodiments of a fractionation method, the concentration of the light component in the isocyanate feed mixture may be from about 5 weight percent or molar percent to about 90 weight percent or molar percent, the concentration of the middle-boiling component in the isocyanate-containing feed mixture may be from about 2 weight percent or molar percent to about 95 weight percent or molar percent, and/or the concentration of the heavy boiling component in the isocyanate-containing feed mixture may be from about 0.1 weight percent or molar percent to about 50 weight percent or molar percent, with the proviso that the concentration of the light component is (i) higher than the middle-boiling component and (ii) higher than the heavy boiling component. According to some embodiments, the middle-boiling component comprises less than about 20 weight percent of the isocyanate feed mixture. The weight or molar ratio of the side section liquid product stream $SdS_{LPS}$ to the isocyanate feed mixture may be more than about 20% in some embodiments. The side section liquid product stream $SdS_{LPS}$, in some embodiments, may comprise an isocyanate (e.g., toluene diisocyanate). The side section liquid product stream $SdS_{LPS}$, in some embodiments, may consist of one or more isocyanates.

According to some embodiments, heating at least a portion of the prefractionating section liquid stream $PS_{LS}$ to form a second prefractionating section vapor stream $sPS_{VS}$ and a second prefractionating section liquid stream $sPS_{LS}$ may comprise heating at least a portion of the prefractionating section liquid stream $PS_{LS}$ in at least one internal reboiler and/or in at least one external reboiler. The prefractionating section, the rectification section, the stripping section, and the side section used to practice a method for fractionating an isocyanate feed mixture, according to some embodiments, may together form a non-adiabatic dividing wall column. In some embodiments, the prefractionating section forms a separate prefractionating column and the rectification section, the stripping section, and the side section together form a separate main column. Moving at least a portion of the rectification section liquid stream $RS_{LS}$ to the prefractionating section may comprise moving the at least a portion of the rectification section liquid stream $RS_{LS}$ to the prefractionating section, wherein the weight or molar ratio of the at least a portion of the rectification section liquid stream $RS_{LS}$ to the prefractionating section vapor stream $PS_{VS}$ may be from about 0 to about 0.75.

A method for fractionating an isocyanate feed mixture may further comprise, according to some embodiments, (s) moving at least a portion of the stripping section vapor stream to the prefractionating section. Moving at least a portion of the stripping section vapor stream to the prefractionating section may comprise moving the at least a portion of the stripping section vapor stream $SS_{VS}$ to the prefractionating section, wherein the weight or molar ratio of the at least a portion of the stripping section vapor stream $SS_{VS}$ to the prefractionating section liquid stream $PS_{LS}$ may be from about 0.01 to about 0.5 in some embodiments.

A method for fractionating an isocyanate feed mixture may comprise, according to some embodiments, maintaining a pressure in the prefractionating section that may be higher than the pressure in the rectification section and/or maintaining a pressure in the fractionating apparatus that may be less than atmospheric pressure. A method for fractionating an isocyanate feed mixture may comprise maintaining at least a portion of the fractionating apparatus at a temperature of from about 50° C. to about 250° C. in some embodiments. A method for fractionating an isocyanate feed mixture may utilize a non-adiabatic fractionating apparatus, according to some embodiments, which consumes from about 0.4 to about 1.0 kilowatts per kilogram of isocyanate produced in the side section liquid product stream $SdS_{LPS}$ and/or consumes less than about 0.4 kilowatts per kilogram of isocyanate produced in the side section liquid product stream $SdS_{LPS}$. A method for fractionating an isocyanate feed mixture may exclude a pretreatment of the isocyanate feed mixture to reduce the ratio of lights in some embodiments.

The present disclosure relates, in some embodiments, to a system for producing an isocyanate. A system may comprise, for example, (a) a phosgene reactor, (b) an isocyante stripper/absorber configured and arranged to remove an acid and excess phosgene and to rectify vapors to minimize isocyante content, (c) a phosgene stripper configured and arranged to recover phosgene, and (d) a non-adiabatic fractionating apparatus.

A non-adiabatic fractionating apparatus may comprise a dividing wall column comprising (1) a prefractionating section comprising an upper and lower end and an intermediate reboiler and (2) a main section in some embodiments. A main section may comprise, according to some embodiments, (i) a rectification section in fluid communication with the upper end of the prefractionating section, (ii) a condenser in fluid communication with the rectification section, (iii) a stripping section in fluid communication with the lower end of the prefractionating section, (iv) a stripping section reboiler in fluid communication with the stripping section, and/or (v) a side section in fluid communication with the rectification section and the stripping section, wherein the fractionating apparatus may be configured and arranged to have a liquid recycle ratio of from about 0.01 to about 0.5 and/or a vapor recycle ratio of from about 0 to about 0.75. A main section may comprise, according to some embodiments, (i) a rectification section in fluid communication with the upper end of the prefractionating section, (ii) a condenser in fluid communication with the rectification section, (iii) a stripping section in fluid communication with the lower end of the prefractionating section, (iv) a stripping section reboiler in fluid communication with the stripping section, and/or (v) a side section in fluid communication with the rectification section and the stripping section, wherein the non-adiabatic fractionating apparatus may be configured and arranged to consume about 0.2 to about 0.4 kilowatts per kilogram of fractionated isocyante produced.

A non-adiabatic fractionating apparatus may comprise (1) a prefractionating column comprising an upper and lower end and an intermediate reboiler and (2) a main column in some embodiments. A main column may comprise, according to some embodiments, (i) a rectification section in fluid communication with the upper end of the prefractionating column, (ii) a condenser in fluid communication with the rectification section, (iii) a stripping section in fluid communication with the lower end of the prefractionating column, (iv) a stripping section reboiler in fluid communication with the stripping section, and/or (v) a side section in fluid communication with the rectification section and the stripping section, wherein the fractionating apparatus may be configured and arranged to have a liquid recycle ratio of from about 0.01 to about 0.5 and/or a vapor recycle ratio of from about 0 to about 0.75. A main column may comprise, according to some embodiments, (i) a rectification section in fluid communication with the upper end of the prefractionating column, (ii) a condenser in fluid communication with the rectification section, (iii) a stripping section in fluid communication with the lower end of the prefractionating column, (iv) a stripping section reboiler in fluid communication with the stripping section, and/or (v) a side section in fluid communication with the rectification section and the stripping section, wherein the non-adiabatic fractionating apparatus may be configured and arranged to consume about 0.2 to about 0.4 kilowatts per kilogram of fractionated isocyante produced. In some embodiments, a system may comprise a distillation feed tank in fluid communication with the phosgene stripper and the prefractionating column.

The present disclosure also relates to a distilled isocyanate obtained by a method of the disclosure. A distilled isocyanate may be made bay a process comprising, for example, (a) contacting an aniline with a phosgene under conditions to form an isocyanate-containing feed mixture (e.g., comprises a light component, a middle-boiling component, and a heavy boiling component), and (b) distilling the isocyanate-containing feed mixture in a non-adiabatic fractionating apparatus. In some embodiments, a non-adiabatic fractionating apparatus may comprise a dividing wall column comprising (1) a prefractionating section comprising an upper and lower end and an intermediate reboiler and (2) a main section. A main section may comprise, according to some embodiments, (i) a rectification section in fluid communication with the upper end of the prefractionating section, (ii) a stripping section in fluid communication with the lower end of the prefractionating section, and/or (iii) a side section in fluid communication with the rectification section and the stripping section, wherein a distilled isocyanate is formed. In some embodiments, a non-adiabatic fractionating apparatus may comprise (1) a prefractionating column comprising an upper and lower end and an intermediate reboiler and (2) a main column. A main column may comprise, according to some embodiments, (i) a rectification section in fluid communication with the upper end of the prefractionating column, (ii) a stripping section in fluid communication with the lower end of the prefractionating column, and/or (iii) a side section in fluid communication with the rectification section and the stripping section, wherein a distilled isocyanate is formed. According to some embodiments, the concentration of the light component may be (i) higher than the middle-boiling component and (ii) higher than the heavy boiling component, wherein the concentration of the light component may be from about 5 weight percent or molar percent to about 90 weight percent or molar percent, the concentration of the middle-boiling component may be from about 2 weight percent or molar percent to about 95 weight percent or molar percent, and the concentration of the heavy boiling component may be from about 0.1 weight percent or molar percent to about 50 weight percent or molar percent.

BRIEF DESCRIPTION OF THE DRAWINGS

Some embodiments of the disclosure may be understood by referring, in part, to the present disclosure and the accompanying drawings, wherein.

DETAILED DESCRIPTION

Figure 1:
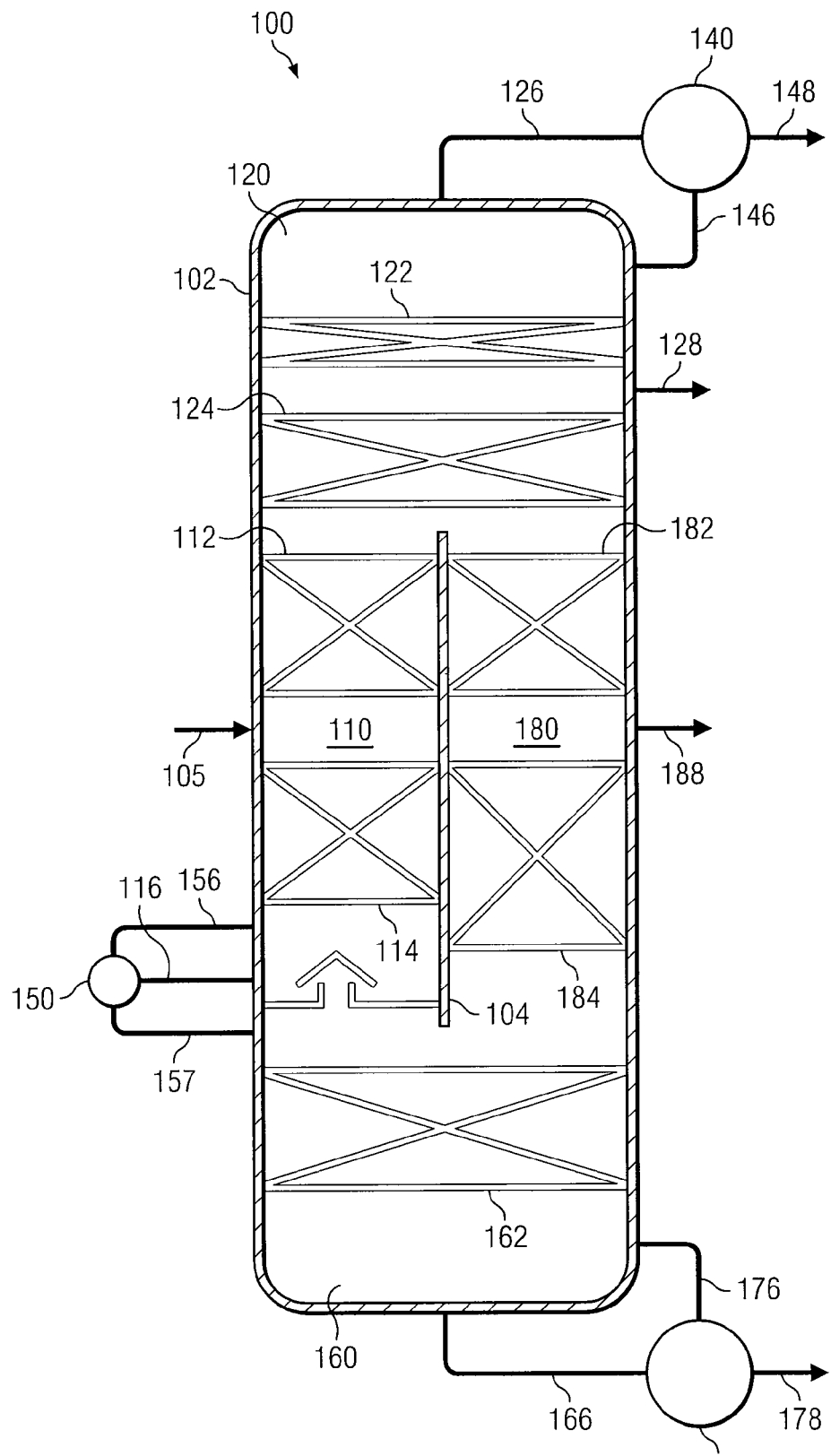
FIG. 1 illustrates a non-adiabatic dividing wall column according to a specific example embodiment of the disclosure.

The present disclosure relates in some embodiments, to apparatus, systems, and methods for fractionating a feed mixture (e.g., a feed mixture comprising one or more isocyanates). Some embodiments of the disclosure may operate with an expanded operating range and/or with higher efficiency than an existing dividing wall column and/or an existing Petlyuk system.

According to some embodiments, fractionating a feed mixture may include separating a complex feed mixture (e.g., a feed mixture containing two or more different chemical species) into one or more fractions, wherein each fraction may contain one of the component species in partially, substantially, and/or completely pure form. For example, a non-adiabatic dividing wall column and/or a modified Petlyuk separation train, in some embodiments, may fractionate a feed mixture with three (3) or more component species into three or more fractions, wherein each fraction may contain one of the three species in partially, substantially, or completely pure form.

An isocyanate mixture may comprise, according to some embodiments, at least one isocyanate. In some embodiments, an isocyanate may comprise at least one isocyanate functional group (i.e., —N=C=O) per isocyanate molecule. For example, an isocyanate may include at least two isocyanate functional groups per isocyanate molecule. Isocyanates may be highly reactive and/or may have a low molecular weight, according to some embodiments. Examples of isocyanates may include, without limitation, hexamethylene diisocyanate (HDI), isophorone diisocyanate (IPDI), methyl isocyanate (MIC), methylene diphenyl diisocyanate (MDI), polymeric methylene diphenyl diisocyanate (PMDI), naphthalene diisocyanate (NDI), toluene diisocyanate (TDI), and the like. An isocyanate feed mixture may comprise an isocyanate mixture, light components, one or more solvents, and/or heavier components. In addition to an isocyanate, an isocyanate feed mixture may also contain a solvent (e.g., ortho-dichlorobenzene), an acid (e.g., HCl), phosgene, carbamoyl chlorides, polymeric isocyanates, and/or combinations thereof.

Apparatus, systems, and/or methods of the disclosure may be adapted, in some embodiments, to separate an isocyanate feed mixture comprising a light component, a middle-boiling component, and a heavy boiling component. In some embodiments, a light component may comprise solvent, hydrochloric acid, phosgene, inert gas (e.g., $N_2$ and/or $CO_2$), and/or combinations thereof. For example, P1 may comprise hydrochloric acid, phosgene, inert gas (e.g., $N_2$ and/or $CO_2$) and/or P2 may comprise or consist of solvent. A middle boiling component may comprise, according to some embodiments, an isocyanate, solvent, and/or combinations thereof. A heavy boiling component may comprise residue, an isocyanate, and/or combinations thereof, in some embodiments.

Apparatus, systems, and/or methods, according to some embodiments, may be configured or adapted to accommodate any solvent. A solvent may have a lower boiling point than a target isocyanate compound(s) in some embodiments. Examples of solvent may include, without limitation, chlorobenzene, ortho-dichlorobenzene, para-dichlorobenzene, trichlorobenzene, a chlorotoluene, a chloroxylene, a chloroethylbenzene, a chloronaphthalene, a chlorobiphenyl, methylene chloride, a perchloroethylene, toluene, a xylene, hexane, a decahydronaphthalene, a carboxylic ester (e.g., diethyl isophthalate), tetrahydrofuran, dimethylformamide, benzene, and combinations thereof.

According to some embodiments, apparatus, systems, and/or methods of the disclosure may be adapted to accommodate a feed mixture having any desired ratio of components and/or having any ratio within a desired range of ratios. For example, an apparatus, system, and/or method of the disclosure may be adapted to effectively separate a mixture (e.g., a three-component mixture), wherein the lightest component constitutes the majority of the mixture (e.g., from about 5 weight percent or molar percent to about 90 weight percent or molar percent). In some embodiments, an apparatus, system, and/or method of the disclosure may be adapted to effectively separate a mixture (e.g., a three-component mixture), wherein a middle-boiling component is present in the feed, for example, at a concentration of from about 2 weight percent or molar percent to about 95 weight percent or molar percent and/or from about 5 weight percent or molar percent to about 75 weight percent or molar percent. An apparatus, system, and/or method of the disclosure may be adapted, in some embodiments, to effectively separate a mixture (e.g., a three-component mixture), wherein a heavy boiling component is present in the feed, for example, at a concentration of from about 0.1 weight percent or molar percent to about 50 weight percent or molar percent.

In some embodiments, an apparatus, system, and/or method of the disclosure may be adapted to effectively separate a mixture (e.g., a three-component mixture), wherein a middle-boiling component is present in the feed at a concentration of, for example, from about 2 weight percent or molar percent to about 5 weight percent or molar percent, from about 2 weight percent or molar percent to about 10 weight percent or molar percent, from about 2 weight percent or molar percent to about 15 weight percent or molar percent, from about 2 weight percent or molar percent to about 18 weight percent or molar percent, from about 2 weight percent or molar percent to about 20 weight percent or molar percent, from about 2 weight percent or molar percent to about 25 weight percent or molar percent, from about 2 weight percent or molar percent to about 50 weight percent or molar percent, from about 2 weight percent or molar percent to about 75 weight percent or molar percent, from about 20 weight percent or molar percent to about 35 weight percent or molar percent, from about 35 weight percent or molar percent to about 55 weight percent or molar percent, from about 55 weight percent or molar percent to about 75 weight percent or molar percent, and/or from about 75 weight percent or molar percent to about 95 weight percent or molar percent. Each of the components in a feed composition may be present in a concentration that is independent of the other components. For example, in a feed mixture comprising A, B, and C, the concentration of A may be the same as or different from the concentration of B and independently the same as or different from the concentration of C (e.g., A=B≠C).

According to some embodiments, apparatus, systems, and/or methods of the disclosure may operate energy efficiently. Energy efficiency metrics may include, for example, energy consumption per unit production (kW/kg). Using this metric, apparatus, systems, and/or methods of the disclosure may operate at an energy consumption per unit production of less than about 0.6 kW/kg, less than about 0.4 kW/kg, less than about 0.38 kW/kg, less than about 0.36 kW/kg, and/or less than about 0.34 kW/kg according to some embodiments. Apparatus, systems, and/or methods of the disclosure may operate, in some embodiments, within a range of from about 0.2 kW/kg to about 0.4 kW/kg, from about 0.25 kW/kg to about 0.4 kW/kg, from about 0.3 kW/kg to about 0.4 kW/kg, from about 0.25 kW/kg to about 0.35 kW/kg, and/or from about 0.28 kW/kg to about 0.38 kW/kg.

Apparatus

According to some embodiments, a fractionating apparatus may comprise a prefractionation column and/or a main distillation column. A prefractionation column and a main distillation column may be combined, in some embodiments, in a single structure (e.g., a dividing wall column).

A fractionating apparatus may comprise a dividing wall column comprising an outer wall defining a dividing wall column volume and an internal vertical wall. An internal vertical wall may be configured and arranged to separate the column volume into two sections, namely a prefractionating section and a main distillation section. A main column section may comprise three sub-sections, namely a rectification section, a stripping section, and a side section. Each section of a dividing wall column may comprise one or more distillation column internals (e.g., trays and/or packing).

A fractionating apparatus may be sized to accommodate any production volume desired, according to some embodiments. For example, a column may have a volume suitable to accommodate industrial and/or commercial quantities of feed. In some embodiments, a fractionating apparatus (e.g., non-adiabatic dividing wall column) may have a total volume of from about one (1) liter to about one million ($10^6$) liters, from about one thousand (1,000) liters to about ten thousand ($10^4$) liters, from about ten thousand ($10^4$) liters to about one hundred thousand ($10^5$) liters, and/or from about one hundred thousand ($10^5$) liters to about one million ($10^6$) liters. The vertical height of a fractionating apparatus column (e.g., non-adiabatic dividing wall column) may be, for example, from about one (1) meter to about one hundred (100) meters. The desired column diameter and volume may influence final selection of a vertical height. For example, a column 30 meters high and 6 meters in diameter would be expected to have a volume of about nine hundred thousand ($9 \times 10^5$) liters.

As shown in the specific example embodiment of FIG. 1, non-adiabatic dividing wall column 100 comprises outer wall 102 defining a generally cylindrical space and vertical dividing wall 104 dividing the space into four sections, namely prefractionating section 110, rectification section 120, stripping section 160, and side section 180, each of which may be in fluid (e.g., vapor and liquid) communication with its adjacent sections. Prefractionating section 110 may be in fluid communication with rectification section 120 and stripping section 160. Rectification section 120 may be in fluid communication with prefractionating section 110 and side section 180. Stripping section 160 may be in fluid communication with prefractionating section 110 and side section 180. Side section 180 may be in fluid communication with rectification section 120 and stripping section 160.

Non-adiabatic dividing wall column 100 further comprises condenser 140, intermediate reboiler 150, and reboiler 170. Condenser 140 may be in fluid (e.g., vapor and liquid) communication with rectification section 120 via line out 126 and return line 146. Intermediate reboiler 150 may be in fluid (e.g., vapor and liquid) communication with prefractionating section 110 via line out 116 and return line 156. Intermediate reboiler 150 also may be in fluid (e.g., vapor and liquid) communication with stripping section 160 via return line 157. Reboiler 170 may be in fluid (e.g., vapor and liquid) communication with stripping section 160 via line out 166 and return line 176.

Separation, according to some embodiments, may be enhanced in each section of the column by using one or more internal trays. For example, as shown in FIG. 1, prefractionating section 110 includes internal trays 112 and 114; rectification section 120 includes internal trays 122 and 124; stripping section 160 includes internal tray 162; and side section 180 includes internal trays 182 and 184. Although illustrated as a single unit, each of these features may comprise two or more stages (e.g., packing and/or trays).

Prefractionating section 110 includes feed inlet 108 through which a distillation feed may be admitted to dividing wall column 100. Condenser 140 includes product outlet 148 through which one or more fractions (e.g., volatile product fractions) may pass out of dividing wall column 100. Rectification section 120 includes product outlet 128 through which one or more fractions (e.g., liquid product fractions) may pass out of dividing wall column 100. Side section 180 includes product outlet 188 through which one or more fractions (e.g., volatile product fractions) may pass out of dividing wall column 100. Reboiler 170 includes product outlet 178 through which one or more fractions (e.g., liquid product fractions) may pass out of dividing wall column 100.

Figure 2:
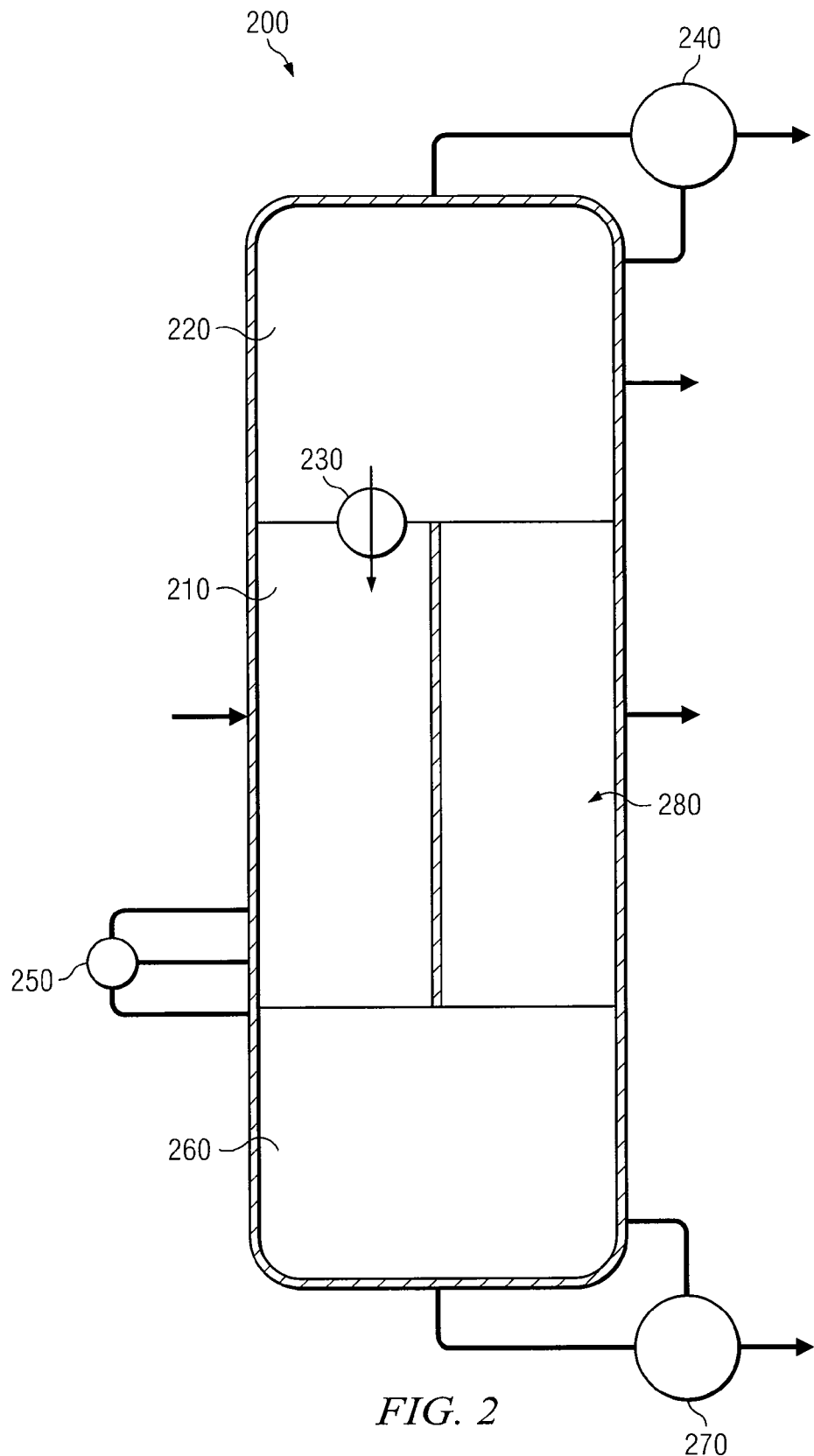
FIG. 2 illustrates a non-adiabatic dividing wall column according to a specific example embodiment of the disclosure.

According to some embodiments, a prefractionating section may have a pressure that is less than atmospheric pressure. A rectification section may have, in some embodiments, a pressure that is lower than the pressure of the prefractionating section such that materials may passively flow from a prefractionating section into a rectification section (with a blower or compressor). As desired or needed, a dividing wall column in which materials move from a rectification section into a prefractionating section may include a pump to raise the pressure of materials in a rectification section to about or above the pressure of the prefractionating section (FIG. 2, pump 230). A fractionating apparatus may further include flow regulators (e.g., valves) that control the flow (e.g., rate, mass, and/or volume) between column sections.

Figure 3:
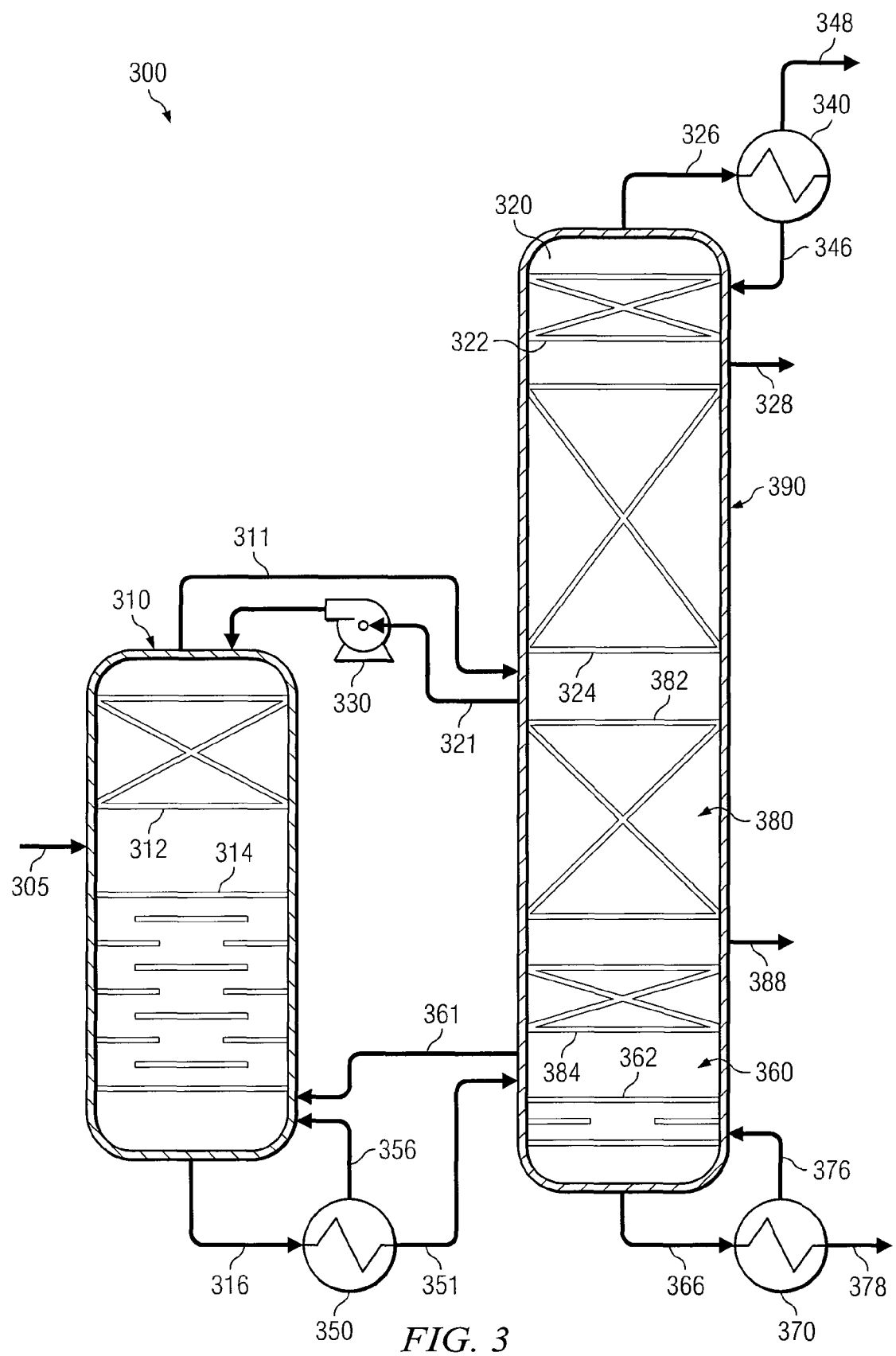
FIG. 3 illustrates a two-column fractionating apparatus according to a specific example embodiment of the disclosure.

As shown in the specific example embodiment of FIG. 3, fractionating apparatus 300 comprises prefractionating column 310 and distillation column 390. Prefractionating column 310 comprises feed inlet 305 configured and arranged to admit a feed. Prefractionating column 310 further comprises packed stage 312, which may comprise one or more stages, and tray 314, which may independently comprise one or more trays. Prefractionating column 310 is fluidically coupled to intermediate reboiler 350 via line out 316 and return line 356.

Distillation column 390 comprises rectification section 320, stripping section 360, and side section 380, each of which may be in fluid (e.g., vapor and liquid) communication with its adjacent sections. Rectification section 320 comprises packed stages 322 and 324. In addition, rectification section 320 is in fluid (e.g., vapor and liquid) communication with condenser 340 via line out 326 and return line 346. Condenser 320 is in fluid (e.g., vapor and liquid) communication with product out 348. Rectification section 320 is in fluid (e.g., vapor and liquid) communication with product out 328. Side section 380 comprises packed stages 382 and 384 and is in fluid (e.g., vapor and liquid) communication with product out 388. Stripping section 360 comprises tray 362 and is in fluid (e.g., vapor and liquid) communication with reboiler 370 via line out 366 and return line 376. Reboiler 370 is in fluid (e.g., vapor and liquid) communication with product out 378.

Prefractionating column 310 may be in fluid (e.g., vapor and liquid) communication with distillation column 390 (e.g., at rectification section 320 and/or stripping section 360). For example, prefractionating column 310 as shown is in fluid (e.g., vapor and liquid) communication with (a) rectification section 320 via line 311 and return line 321 and (b) stripping section 360 via line 351 and return line 361. Return line 321 is fluidically coupled to pump 330.

Figure 4:
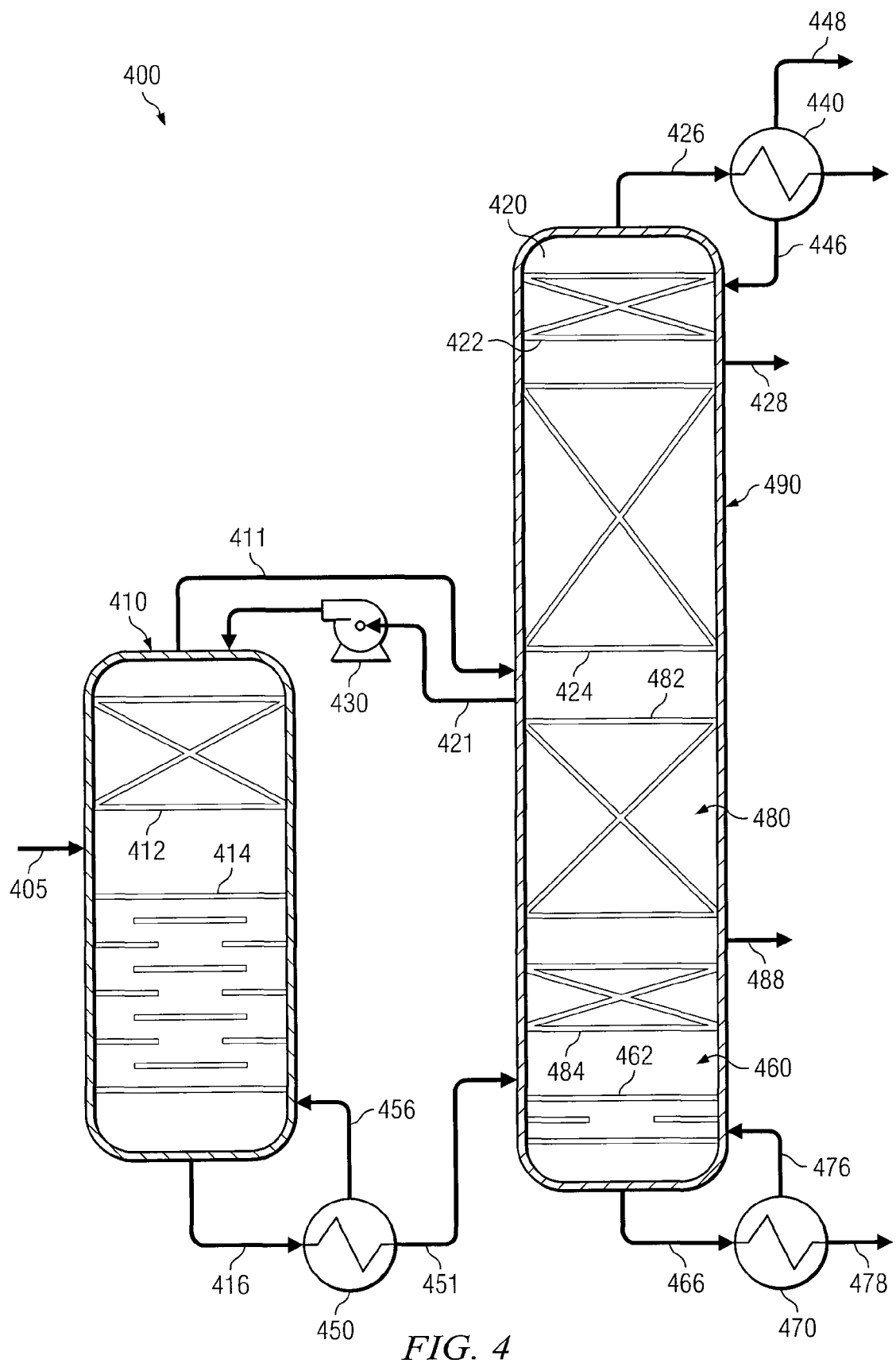
FIG. 4 illustrates a two-column fractionating apparatus according to a specific example embodiment of the disclosure.

As shown in the specific example embodiment of FIG. 4, fractionating apparatus 400 comprises prefractionating column 410 and distillation column 490. Prefractionating column 410 comprises feed inlet 405 configured and arranged to admit a feed. Prefractionating column 410 further comprises packed stage 412, which may comprise one or more stages, and tray 414, which may independently comprise one or more trays. Prefractionating column 410 is fluidically coupled to intermediate reboiler 450 via line out 416 and return line 456.

Distillation column 490 comprises rectification section 420, stripping section 460, and side section 480, each of which may be in fluid (e.g., vapor and liquid) communication with its adjacent sections. Rectification section 420 comprises packed stages 422 and 424. In addition, rectification section 420 is in fluid (e.g., vapor and liquid) communication with condenser 440 via line out 426 and return line 446. Condenser 420 is in fluid (e.g., vapor and liquid) communication with product out 448. Rectification section 420 is in fluid (e.g., vapor and liquid) communication with product out 428. Side section 480 comprises packed stages 482 and 484 and is in fluid (e.g., vapor and liquid) communication with product out 488. Stripping section 460 comprises tray 462 and is in fluid (e.g., vapor and liquid) communication with reboiler 470 via line out 466 and return line 476. Reboiler 470 is in fluid (e.g., vapor and liquid) communication with product out 478.

Prefractionating column 410 may be in fluid (e.g., vapor and liquid) communication with distillation column 490 (e.g., at rectification section 420 and/or stripping section 460). For example, prefractionating column 410 as shown is in fluid (e.g., vapor and liquid) communication with (a) rectification section 420 via line 411 and return line 421 and (b) stripping section 460 via line 451. Return line 421 is fluidically coupled to pump 430.

Any suitable materials may be used to prepare a fractionating apparatus, in some embodiments. For example, a dividing wall column, a prefractionating column, and/or a main column may comprise a carbon steel, a stainless steel, and/or an alloy (e.g., INCONEL™)

Systems

According to some embodiments, a system may comprise up to a complete system for producing isocyanate(s) and a fractionating apparatus. A system may comprise a fractionating apparatus and up to a complete system for producing polyurethane(s) in some embodiments. A system, according to some embodiments, may comprise up to a complete system for producing isocyanate(s), a fractionating apparatus, and up to a complete system for producing polyurethane(s).

A system for producing isocyante(s) may comprise a phosgene reactor, an isocyante stripper/absorber (e.g., to remove HCl and excess phosgene and rectify vapors to minimize isocyante content), and a phosgene stripper (e.g., for recovery of phosgene). For example, a system may include (i) a fractionating apparatus and (ii) a phosgene reactor, an isocyante stripper/absorber, a phosgene stripper, a distillation feed tank, and/or a crude product flasher (e.g., to remove as much residue as possible before entering a fractionating apparatus).

A system for producing polyurethane(s) may comprise an isocyanate fractionating apparatus and a foam mixing head in fluid communication with the isocyanate fractionating apparatus (e.g., at a side section outlet), the foam mixing head comprising a manifold with inlets for isocyanates, polyols, additives, and air. A system may comprise an isocyanate storage tank, according to some embodiments.

Methods

A method of fractionating a feed mixture, according to some embodiments, may be carried out using a dividing wall column fractionating apparatus comprising a prefractionating section, a rectification section, a side section, and/or a stripping section. In some embodiments, a method of fractionating a feed mixture may be carried out using an apparatus comprising a prefractionating column and/or a main column, wherein the main column may comprise a rectification section, a side section, and/or a stripping section. Accordingly, for the purpose of describing some embodiments of fractionating methods of the disclosure, a prefractionating section may refer to a prefractionating section of a dividing wall column and/or a prefractionating column.

Prefractionating Section

A method of fractionating a feed mixture, according to some embodiments, may comprise actively and/or passively moving a feed mixture F1 (e.g., an isocyanate feed mixture) into a fractionating apparatus (e.g., a prefractionating section of a dividing wall column and/or a prefractionating column). In some embodiments, a method may comprise heating the contents of a prefractionating section (e.g., a feed mixture F1) to form a prefractionating section vapor stream $PS_{VS}$ and a prefractionating section liquid stream $PS_{LS}$. A method may comprise, according to some embodiments, heating at least a portion of a prefractionating section liquid stream $PS_{LS}$ (e.g., in a contiguous and/or separate reboiler) to form a second prefractionating section vapor stream $sPS_{VS}$ and a second prefractionating section liquid stream $sPS_{LS}$, which may be actively and/or passively combined with the first prefractionating section vapor stream $PS_{VS}$ and the first prefractionating section liquid stream $PS_{LS}$, respectively. This may occur, for example, in the prefractionating section itself, at or near the junction between the prefractionating section and the rectification section (e.g., $PS_{VS}$), or at or near the junction between the prefractionating section and the stripping section (e.g., $PS_{LS}$).

Rectification Section

A method may comprise actively and/or passively moving a prefractionating section vapor stream $PS_{VS}$ from a prefractionating section to a rectification section (e.g., of a dividing wall column and/or a main column) and actively and/or passively cooling the prefractionating section vapor stream $PS_{VS}$ to form a rectification section vapor product stream $RS_{VPS}$ and a condensate liquid, in some embodiments. At least a portion of a condensate liquid may form, according to some embodiments, a rectification section liquid product stream $RS_{LPS}$. In some embodiments, a method may comprise removing (e.g., actively and/or passively removing) a rectification section liquid product stream $RS_{LPS}$ from a rectification section. At least a portion of a condensate liquid may form a rectification section liquid stream $RS_{LS}$, according to some embodiments. A method of fractionating a feed mixture, in some embodiments, may comprise moving (e.g., actively and/or passively moving) at least a portion of a rectification section liquid stream $RS_{LS}$ to a side section (e.g., of a dividing wall column and/or a main column). In some embodiments, a method of fractionating a feed mixture may comprise moving (e.g., actively and/or passively moving) at least a portion of a rectification section liquid stream $RS_{LS}$ to the prefractionating section.

Stripping Section

A method may comprise actively and/or passively moving a prefractionating section liquid stream $PS_{LS}$ from a prefractionating section to a stripping section (e.g., of a dividing wall column and/or a main column), in some embodiments. A method may comprise, according to some embodiments, heating the contents of a stripping section (e.g., a prefractionating section liquid stream $PS_{LS}$) to form a stripping section vapor stream $SS_{VS}$ and a stripping section lower product stream $SS_{LPS}$ (which may be actively and/or passively removed from the fractionating apparatus). In some embodiments, a method of fractionating a feed mixture may comprise moving (e.g., actively and/or passively moving) at least a portion of a stripping section vapor stream $SS_{VS}$ to a side section (e.g., of a dividing wall column and/or a main column). A method may comprise moving (e.g., actively and/or passively moving) at least a portion of a stripping section vapor stream $SS_{VS}$ to a prefractionating section, according to some embodiments.

Side Section

A method of fractionating a feed mixture may comprise, in some embodiments, comingling at least a portion of a rectification section liquid stream $RS_{LS}$ and at least a portion of a stripping section vapor stream $SS_{VS}$ in a side section under conditions that permit formation of a side section vapor stream $SdS_{VS}$, a side section liquid product stream $SdS_{LPS}$, and/or a side section liquid stream $SdS_{LS}$. According to some embodiments, a method may comprise moving (e.g., actively and/or passively moving) at least a portion of a side section vapor stream $SdS_{VS}$ to a rectification section. A method of fractionating a feed mixture may comprise removing (e.g., actively and/or passively removing) at least a portion of a side section liquid product stream $SdS_{LPS}$ from the fractionating apparatus, in some embodiments. A method may comprise, according to some embodiments, moving (e.g., actively and/or passively moving) at least a portion of a side section liquid stream $SdS_{LS}$ to a stripping section.

Each of the foregoing steps may be independently performed (active) or permitted (passive) according to some embodiments. For example, cooling may comprise actively lowering the temperature of a material (e.g., using refrigeration equipment) or passively allowing a material to progress toward equilibrium with its surroundings (e.g., ambient temperature).

Figure 5:
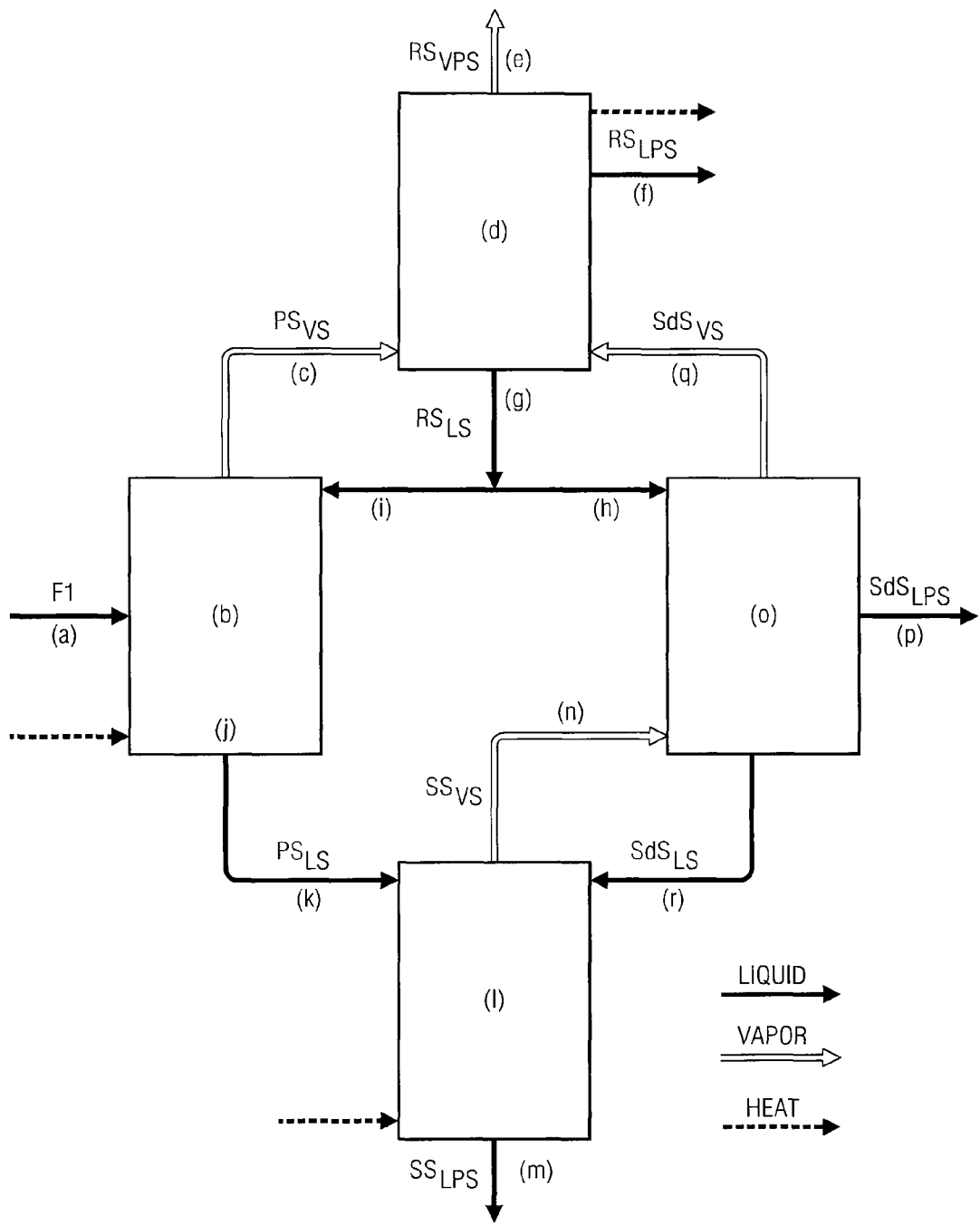
FIG. 5 illustrates a flow chart of a fractionation method according to a specific example embodiment of the disclosure.

A specific example embodiment of a method of fractionating a feed mixture may comprise, as illustrated in FIG. 5, (a) moving the feed mixture (e.g., an isocyanate feed mixture) F1 into a fractionating apparatus (e.g., a prefractionating section of a dividing wall column and/or a prefractionating column), (b) warming the contents of the prefractionating section/column and forming a prefractionating section vapor stream $PS_{VS}$ and a prefractionating section liquid stream $PS_{LS}$, (c) moving at least a portion of the prefractionating section vapor stream $PS_{VS}$ to a rectification section (e.g., of a dividing wall column and/or a main column), (d) cooling the contents of the rectification section (e.g., at least a portion of the prefractionating section vapor stream $PS_{VS}$) to form a rectification section vapor product stream $RS_{VPS}$ and a condensate liquid, (e) removing from the fractionating apparatus at least a portion of the rectification section vapor product stream $RS_{VPS}$, (f) removing from the fractionating apparatus at least a portion of the condensate liquid as a rectification section liquid product stream $RS_{LPS}$, (g) removing from the rectification section at least a portion of the condensate liquid as a rectification section liquid stream $RS_{LS}$, (h) moving at least a portion of the rectification section liquid stream $RS_{LS}$ to a side section (e.g., of a dividing wall column and/or a main column), (i) moving at least a portion of the rectification section liquid stream $RS_{LS}$ to the prefractionating section, (j) optionally heating at least a portion of the prefractionating section liquid stream $PS_{LS}$ (e.g., in a contiguous and/or separate reboiler) to form a second prefractionating section vapor stream $sPS_{VS}$ and a second prefractionating section liquid stream $sPS_{LS}$ and combining each with their respective first streams (not expressly shown), (k) moving at least a portion of the prefractionating section liquid stream $PS_{LS}$ from the prefractionating section/column to a stripping section (e.g., of a dividing wall column and/or a main column), (l) heating the contents of the stripping section (e.g., at least a portion of the prefractionating section liquid stream $PS_{LS}$) to form a stripping section vapor stream $SS_{VS}$ and a stripping section lower product stream $SS_{LPS}$, (m) removing from the fractionating apparatus at least a portion of the stripping section liquid stream $SS_{VS}$ to the side section, (o) comingling at least a portion of the rectification section liquid stream $RS_{LS}$ and at least a portion of the stripping section vapor stream $SS_{VS}$ in the side section under conditions that permit formation of a side section vapor stream $SdS_{VS}$, a side section liquid product stream $SdS_{LPS}$, and/or a side section liquid stream $SdS_{LS}$, (p) removing from the fractionating apparatus at least a portion of the side section liquid product stream $SdS_{LPS}$, (q) moving at least a portion of the side section vapor stream $SdS_{VS}$ to the rectification section, and (r) moving at least a portion of the side section liquid stream $SdS_{LS}$ to the stripping section.

Figure 6:
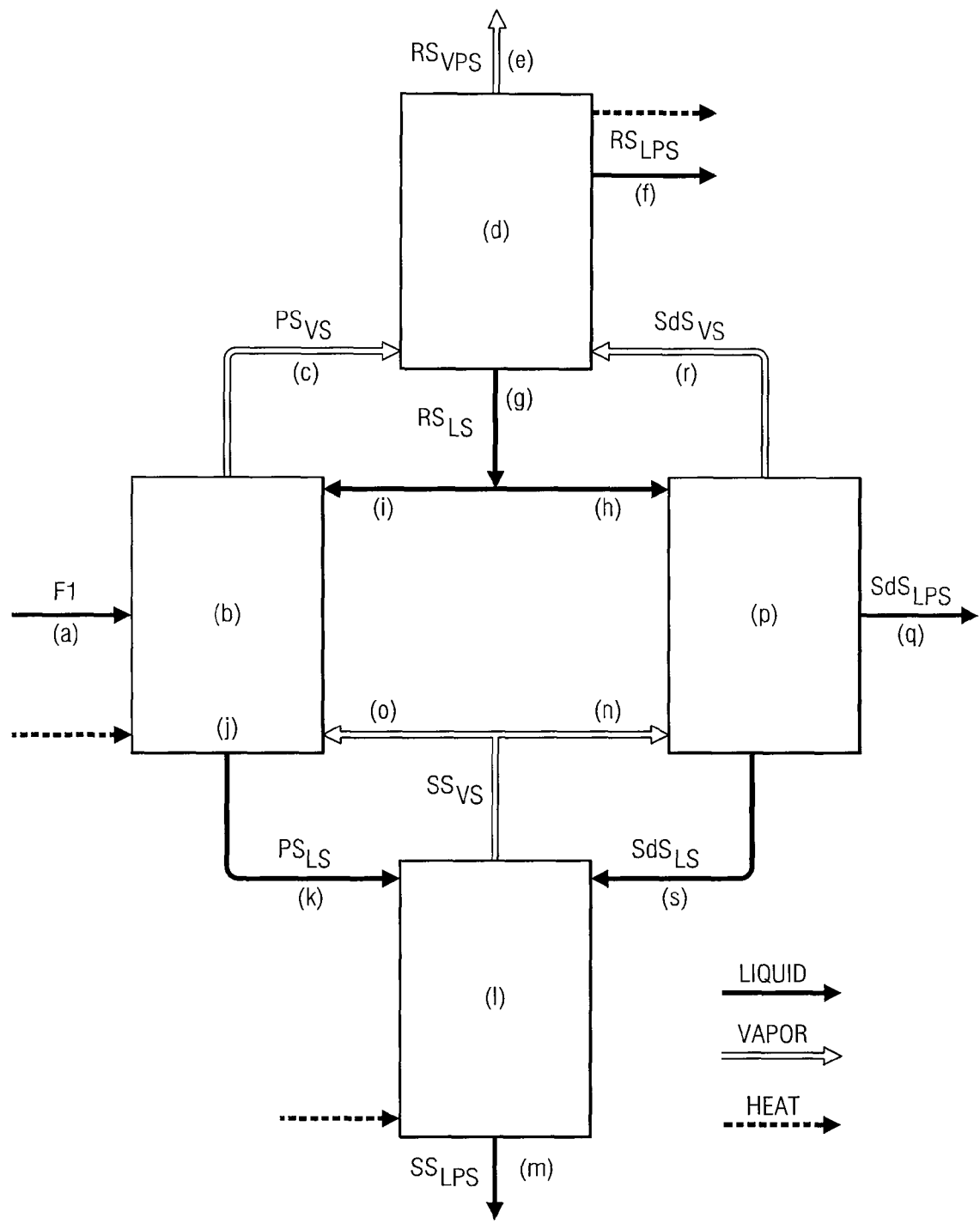
FIG. 6 illustrates a flow chart of a fractionation method according to a specific example embodiment of the disclosure.

A specific example embodiment of a method of fractionating a feed mixture may comprise, as illustrated in FIG. 6, (a) moving the feed mixture (e.g., an isocyanate feed mixture) F1 into a fractionating apparatus (e.g., a prefractionating section of a dividing wall column and/or a prefractionating column), (b) warming the contents of the prefractionating section/column and forming a prefractionating section vapor stream $PS_{VS}$ and a prefractionating section liquid stream $PS_{LS}$, (c) moving at least a portion of the prefractionating section vapor stream $PS_{VS}$ to a rectification section (e.g., of a dividing wall column and/or a main column), (d) cooling the contents of the rectification section (e.g., at least a portion of the prefractionating section vapor stream $PS_{VS}$) to form a rectification section vapor product stream $RS_{VPS}$ and a condensate liquid, (e) removing from the fractionating apparatus at least a portion of the rectification section vapor product stream $RS_{VPS}$, (f) removing from the fractionating apparatus at least a portion of the condensate liquid as a rectification section liquid product stream $RS_{LPS}$, (g) removing from the rectification section at least a portion of the condensate liquid as a rectification section liquid stream $RS_{LS}$, (h) moving at least a portion of the rectification section liquid stream $RS_{LS}$ to a side section (e.g., of a dividing wall column and/or a main column), (i) moving at least a portion of the rectification section liquid stream $RS_{LS}$ to the prefractionating section, (j) optionally heating at least a portion of the prefractionating section liquid stream $PS_{LS}$ (e.g., in a contiguous and/or separate reboiler) to form a second prefractionating section vapor stream $sPS_{VS}$ and a second prefractionating section liquid stream $sPS_{LS}$ and combining each with their respective first streams (not expressly shown), (k) moving at least a portion of the prefractionating section liquid stream $PS_{LS}$ from the prefractionating section/column to a stripping section (e.g., of a dividing wall column and/or a main column), (l) heating the contents of the stripping section (e.g., at least a portion of the prefractionating section liquid stream $PS_{LS}$) to form a stripping section vapor stream $SS_{VS}$ and a stripping section lower product stream $SS_{LPS}$, (m) removing from the fractionating apparatus at least a portion of the stripping section liquid product stream $SS_{LPS}$, (n) moving at least a portion of the stripping section vapor stream $SS_{VS}$ to the side section, (o moving at least a portion of the stripping section vapor stream $SS_{VS}$ to the prefractionating section/column, (p) comingling at least a portion of the rectification section liquid stream $RS_{LS}$ and at least a portion of the stripping section vapor stream $SS_{VS}$ in the side section under conditions that permit formation of a side section vapor stream $SdS_{VS}$, a side section liquid product stream $SdS_{LPS}$, and/or a side section liquid stream $SdS_{LS}$, (q) removing from the fractionating apparatus at least a portion of the side section liquid product stream $SdS_{LPS}$, (r) moving at least a portion of the side section vapor stream $SdS_{VS}$ to the rectification section, and (s) moving at least a portion of the side section liquid stream $SdS_{LS}$ to the stripping section. According to a specific example embodiment, the composition of one or more of these streams may be as shown in Table 1.

TABLE 1

Specific Example Embodiment of Stream Composition

| Stream | Phase | Composition |
|---|---|---|
| F1 | liquid | Mixture of isocyanate, solvent, light and heavy components |
| Prefractionating section/column | | |
| $PS_{VS}$ | vapor | Mixture of isocyanate, solvent, light without heavy components |

TABLE 1-continued

Specific Example Embodiment of Stream Composition

| Stream | Phase | Composition |
|---|---|---|
| $PS_{LS}$ | liquid | Mixture of isocyanate, solvent, heavy components without light components |
| Rectification section | | |
| $RS_{VPS}$ | vapor | Lights and non-condensable components |
| $RS_{LPS}$ | liquid | Solvent (e.g., ODCB) free of non-condensable components with traces of isocyanate |
| $RS_{LS}$ | liquid | Mixture of isocyanate, solvent without light and heavy components |
| Stripping section | | |
| $SS_{VS}$ | vapor | Mixture of isocyanate, solvent, with traces of heavy components without light components |
| $SS_{LPS}$ | liquid | Mixture of isocyanate, solvent, with heavy components |
| Side section | | |
| $SdS_{VS}$ | vapor | Mixture of isocyanate, solvent without light and heavy components |
| $SdS_{LPS}$ | liquid | Isocyanate (e.g., TDI) |
| $SdS_{LS}$ | liquid | Mixture of isocyanate, solvent and heavy components |

Figure 7:
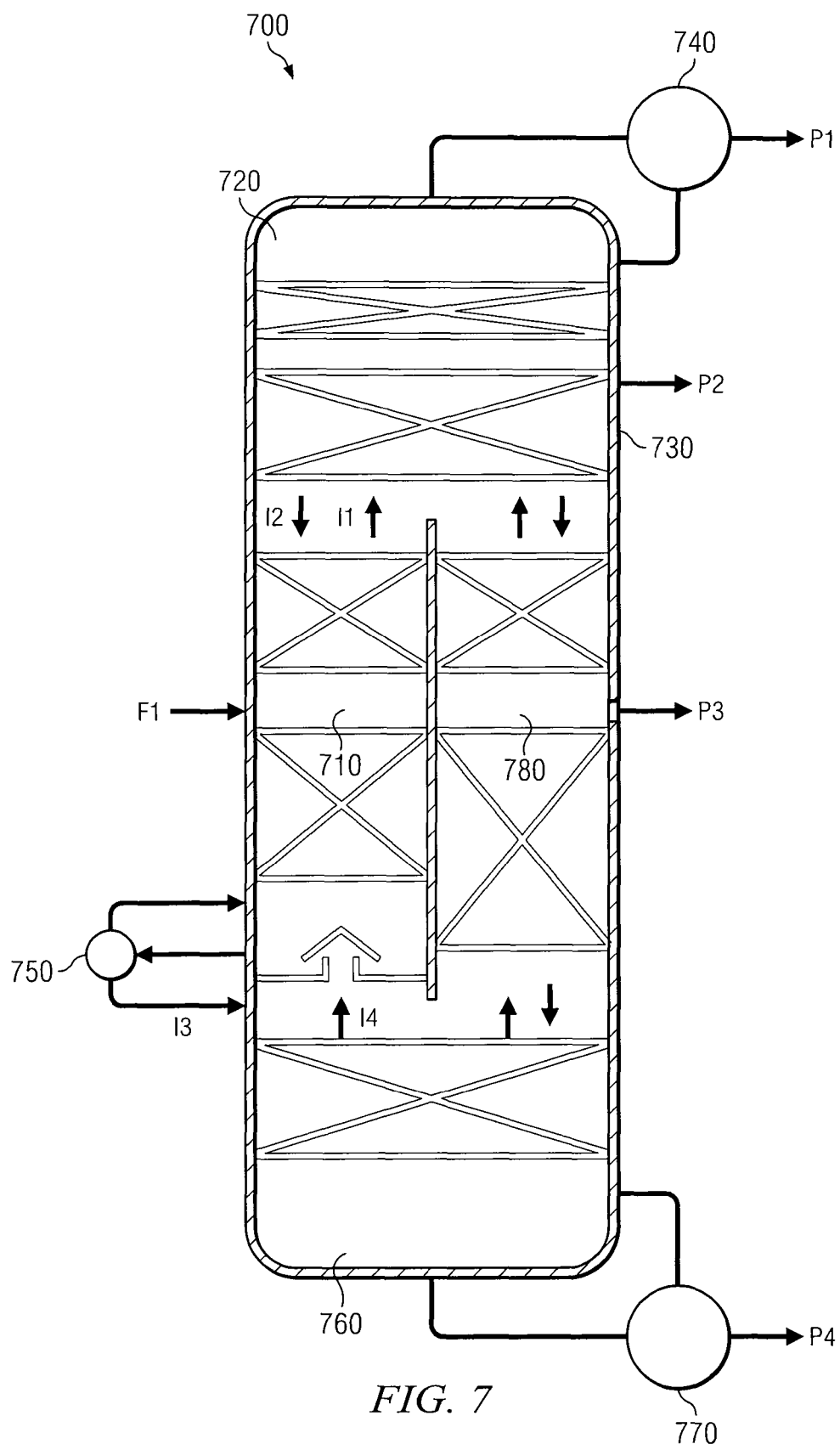
FIG. 7 illustrates a non-adiabatic dividing wall column according to a specific example embodiment of the disclosure.

A specific example embodiment of a method of fractionating a feed mixture may comprise, as illustrated in FIG. 7, (a) moving feed mixture (e.g., an isocyanate feed mixture) F1 into prefractionating section 710 of non-adiabatic dividing wall column 700, (b) warming the contents of prefractionating section 710 and forming an internal stream I1 (vapor) and a prefractionating section liquid stream, (c) moving at least a portion of the internal stream I1 to rectification section 720, (d) cooling at least a portion of the contents of rectification section 720 using condenser 740 to form a rectification section vapor product stream P1 and a condensate liquid, (e) removing from fractionating apparatus 700 at least a portion of the rectification section vapor product stream P1, (f) removing from fractionating apparatus 700 at least a portion of the condensate liquid as a rectification section liquid product stream P2, (g) moving from rectification section 720 to prefractionating section 710 at least a portion of the condensate liquid as internal stream I2, (h) moving from rectification section 720 to side section 780 at least a portion of the condensate liquid, (i) optionally heating at least a portion of the contents of prefractionating section 710 using external intermediate reboiler 750 to form an intermediate reboiler vapor stream and internal stream I3 (liquid), (j) returning the intermediate reboiler vapor stream and the internal stream I3 (liquid) to prefractionating section 710, (k) moving at least a portion of the prefractionating section liquid stream from prefractionating section 710 to stripping section 760, (l) heating the contents of stripping section 760 using reboiler 770 to form a stripping section vapor stream a stripping section product stream (liquid) P4, (m) removing from the fractionating apparatus at least a portion of the stripping section product stream (liquid) P4, (n) moving at least a portion of the stripping section vapor stream to side section 780, (o) moving at least a portion of the stripping section vapor stream to prefractionating section 710 as internal stream I4, (p) comingling in side section 780 at least a portion of the condensate liquid moved to side section 780 and at least a portion of the stripping section vapor stream moved to side section 780 under conditions that permit formation of a side section vapor stream, a side section product stream P3 (liquid), and a side section liquid stream, (q) removing from fractionating apparatus 700 at least a portion of side section product stream P3, (r) moving at least a portion of the side section vapor stream to rectification section 720, and (s) moving at least a portion of the side section liquid stream to stripping section 760.

In some embodiments, a portion of feed F1 may split off to form internal vapor stream I1, which may move (e.g., actively and/or passively) to rectification section 720, where lights and non-condensable components may be rectified as top product P1 through condenser 740. Solvent (e.g., mainly ortho dichloro benzene free of light non-condensable components and/or containing traces of isocyanate) may be removed from rectification section 720 (e.g., from second theoretical stage 730 of main rectification section 720) as product P2. A liquid bottom portion of feed F1 may move (e.g., actively and/or passively) through intermediate reboiler 750 to form internal stream I3. Internal stream I3 may exit intermediate reboiler 750 and enter main stripping section 760, where most of the isocyanate (e.g., TDI) and lighter components may be stripped from the liquid. The remaining, stripped liquid may leave stripping section 760 as bottom product P4 through reboiler 770. At least a portion of the vapor from stripping section 760 containing isocyanate and lighter components (internal stream I4) may enter (reenter) prefractionating section 710 through a chimney tray. At least a portion of the vapor from stripping section 760 may enter side section 780. In side section 780 the isocyanate (e.g., TDI) may be removed as main product P3.

Figure 8:
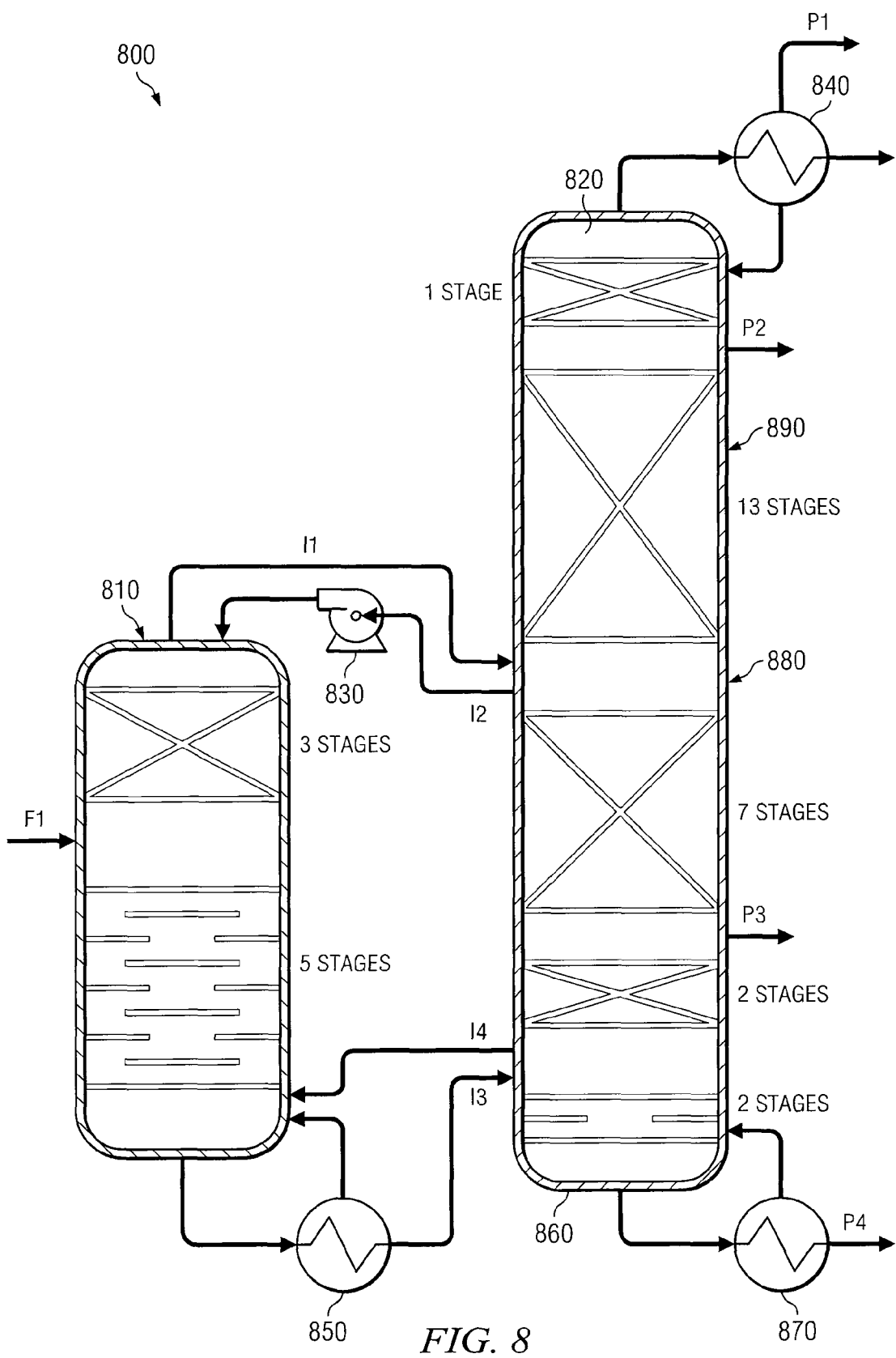
FIG. 8 illustrates a two-column fractionating apparatus according to a specific example embodiment of the disclosure.

A specific example embodiment of a method of fractionating a feed mixture may comprise, as illustrated in FIG. 8, (a) moving feed mixture (e.g., an isocyanate feed mixture) F1 into prefractionating column 810 of fractionating apparatus 800, (b) warming the contents of prefractionating column 810 and forming an internal stream I1 (vapor) and a prefractionating section liquid stream, (c) moving at least a portion of the internal stream I1 to main column 890, (d) cooling at least a portion of the contents of rectification section 820 using condenser 840 to form a rectification section vapor product stream P1 and a condensate liquid, (e) removing from main column 890 at least a portion of the rectification section vapor product stream P1, (f) removing from main column 890 at least a portion of the condensate liquid as a rectification section liquid product stream P2, (g) moving from main column 890 to prefractionating column 810 at least a portion of the condensate liquid as internal stream I2 using pump 830, (h) moving from rectification section 820 to side section 880 at least a portion of the condensate liquid, (i) optionally heating at least a portion of the contents of prefractionating column 810 using external intermediate reboiler 850 to form an intermediate reboiler vapor stream and internal stream I3 (liquid), (j) returning the intermediate reboiler vapor stream to prefractionating column 810, (k) moving at least a portion of internal stream I3 (liquid) to stripping section 860, (l) heating the contents of stripping section 860 using reboiler 870 to form a stripping section vapor stream a stripping section product stream (liquid) P4, (m) removing from fractionating apparatus at least a portion of the stripping section product stream (liquid) P4, (n) moving at least a portion of the stripping section vapor stream to side section 880, (o) moving at least a portion of the stripping section vapor stream to prefractionating column 810 as internal stream I4, (p) comingling in side section 880 at least a portion of the condensate liquid moved to side section 880 and at least a portion of the stripping section vapor stream moved to side section 880 under conditions that permit formation of a side section vapor stream, a side section product stream P3 (liquid), and a side section liquid stream, (q) removing from fractionating apparatus 800 at least a portion of side section product stream P3, (r) moving at least a portion of the side section vapor stream to rectification section 820, and (s) moving at least a portion of the side section liquid stream to stripping section 860.

According to some embodiments, feed F1 may enter fractionating apparatus 800 at prefractionating column 810, which has at least one external (shown) reboiler 850. Internal vapor stream I1 may move (e.g., actively and/or passively) to rectification section 820 of main column 890, where lights and non-condensable components may be rectified as top product P1 through condenser 840. Solvent (e.g., mainly ortho dichloro benzene free of light non-condensable components and/or containing traces of isocyanate) may be removed from main rectification section 820 (e.g., from second theoretical stage rectification section 820) as product P2. A liquid bottom portion of feed F1 may move (e.g., actively and/or passively) through intermediate reboiler 850 to form internal stream I3. Internal stream I3 may exit intermediate reboiler 850 and enter main stripping section 860, where most of the isocyanate (e.g., TDI) and lighter components are stripped from the liquid. The remaining, stripped liquid may leave stripping section 860 as bottom product P4 through reboiler 870. At least a portion of the vapor from stripping section 860 containing isocyanate and lighter components (internal stream I4) may enter (reenter) prefractionating column 810. At least a portion of the vapor from stripping section 860 may enter side section 880. This entry/reentry may include using a blower or compressor according to some embodiments. In side section 880 the isocyanate (e.g., TDI) may be removed as main product P3.

Figure 9:
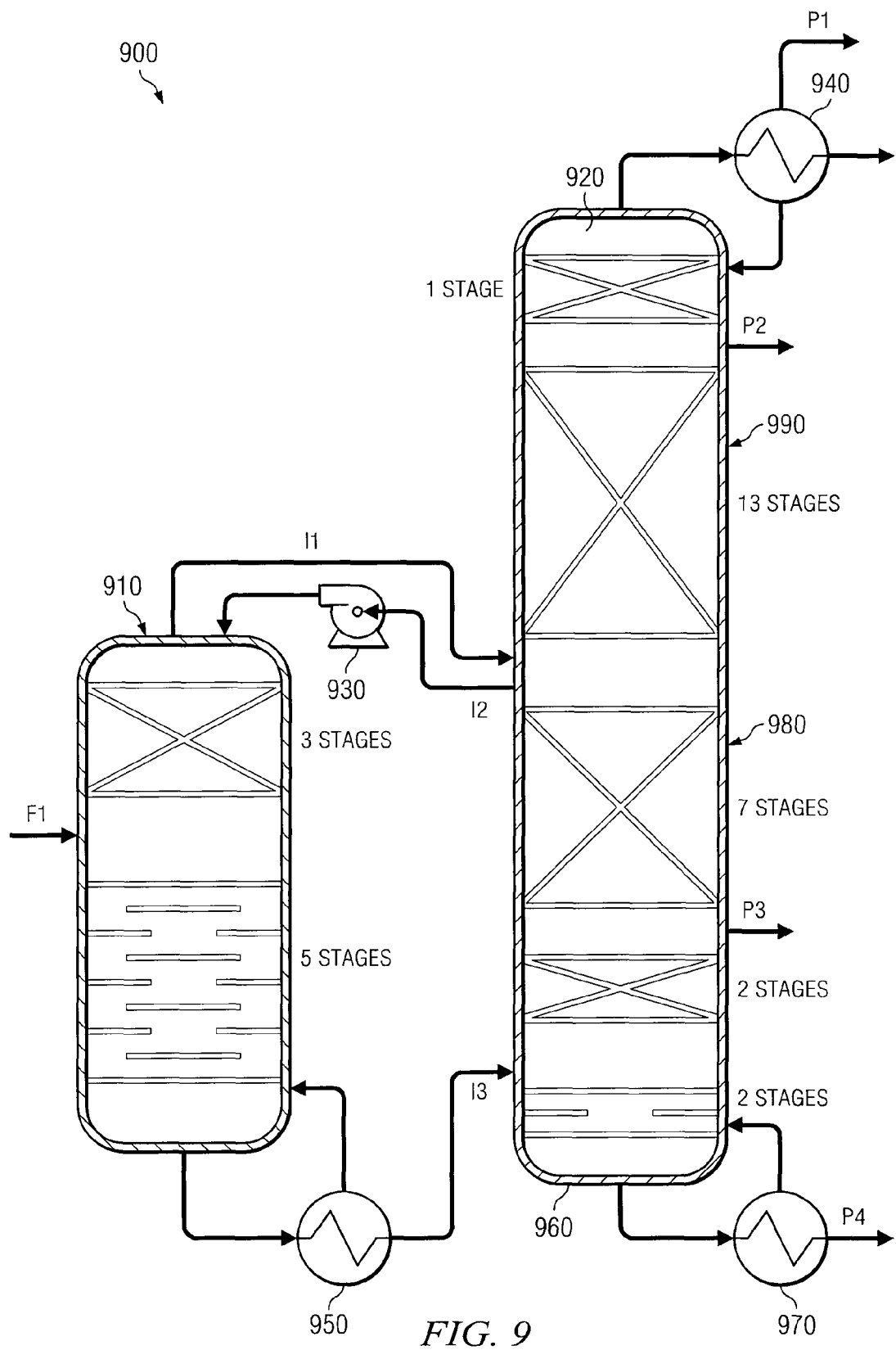
FIG. 9 illustrates a two-column fractionating apparatus according to a specific example embodiment of the disclosure.

A specific example embodiment of a method of fractionating a feed mixture may comprise, as illustrated in FIG. 9, (a) moving feed mixture (e.g., an isocyanate feed mixture) F1 into prefractionating column 910 of fractionating apparatus 900, (b) warming the contents of prefractionating column 910 and forming an internal stream I1 (vapor) and a prefractionating section liquid stream, (c) moving at least a portion of the internal stream I1 to main column 990, (d) cooling at least a portion of the contents of rectification section 920 using condenser 940 to form a rectification section vapor product stream P1 and a condensate liquid, (e) removing from main column 990 at least a portion of the rectification section vapor product stream P1, (l) removing from main column 990 at least a portion of the condensate liquid as a rectification section liquid product stream P2, (g) moving from main column 990 to prefractionating column 910 at least a portion of the condensate liquid as internal stream I2 using pump 930, (h) moving from rectification section 920 to side section 980 at least a portion of the condensate liquid, (i) optionally heating at least a portion of the contents of prefractionating column 910 using external intermediate reboiler 950 to form an intermediate reboiler vapor stream and internal stream I3 (liquid), (j) returning the intermediate reboiler vapor stream to prefractionating column 910, (k) moving at least a portion of internal stream I3 (liquid) to stripping section 960, (l) heating the contents of stripping section 960 using reboiler 970 to form a stripping section vapor stream a stripping section product stream (liquid) P4, (m) removing from fractionating apparatus at least a portion of the stripping section product stream (liquid) P4, (n) moving at least a portion of the stripping section vapor stream to side section 980, (o) comingling in side section 980 at least a portion of the condensate liquid moved to side section 980 and at least a portion of the stripping section vapor stream moved to side section 980 under conditions that permit formation of a side section vapor stream, a side section product stream P3 (liquid), and a side section liquid stream, (p) removing from fractionating apparatus 900 at least a portion of side section product stream P3, (q) moving at least a portion of the side section vapor stream to rectification section 920, and (r) moving at least a portion of the side section liquid stream to stripping section 960.

In some embodiments, feed F1 may enter fractionating apparatus 900 at prefractionating column 910, which may have at least one external reboiler 950. Internal vapor stream I1 may move (e.g., actively and/or passively) to rectification section 920 of main column 990, where lights and non-condensable components may be rectified as top product P1 through condenser 940. Solvent (e.g., mainly ortho dichloro benzene free of light non-condensable components and/or containing traces of isocyanate) may be removed from main rectification section 920 (e.g., from second theoretical stage rectification section 920) as product P2. A liquid bottom portion of feed F1 may move (e.g., actively and/or passively) through intermediate reboiler 950 to form internal stream I3. Internal stream I3 may exit intermediate reboiler 950 and enter main stripping section 960, where most of the isocyanate (e.g., TDI) and lighter components may be stripped from the liquid. The remaining, stripped liquid may leave stripping section 960 as bottom product P4 through reboiler 970. The vapor from stripping section 960 containing isocyanate and lighter components may move (e.g., actively and/or passively) to side section 980. In side section 980 the isocyanate (e.g., TDI) may be removed as main product P3.

In some embodiments, each stream (e.g., an internal stream or a product stream) may be collected independently in a single fraction or multiple fractions. Where a stream is collected across two or more fractions, the fractions may be pooled as desired or required.

A prefractionating column and a main column may be contained in a common structure (e.g., within a single housing). For example, a combined prefractionating/main column may be configured and arranged as a dividing wall column (e.g., a non-adiabatic dividing wall column). In some embodiments, fractionating a distillation feed may comprise establishing and/or maintaining a pressure drop across a column (e.g., between F1 and P1, P2, P3, and/or P4) and/or a portion thereof (e.g., between the top and bottom of a prefractionating section) of from about 0 mm Hg to about 50 mm Hg. Fractionating a distillation feed may comprise establishing and/or maintaining a pressure less than about atmospheric pressure in at least a portion of a column, according to some embodiments. For example, fractionating a feed mixture may comprise establishing and/or maintaining a column (prefractionating and/or main column) pressure from about 10 mm Hg to about 500 mm Hg, from about 15 mm Hg to about 200 mm Hg, from about 20 mm Hg to about 60 mm Hg The pressure may depend on the solvent(s) present and/or column configuration. For example, pressure in a single column may be from about 30 mm Hg to about 60 mm Hg while pressure in a two-column apparatus may be about 145 mm Hg in the first column and from about 20 mm Hg to about 25 mm Hg in the second. The pressure at the top of a prefractionating column may be higher than the pressure in a rectification section, according to some embodiments, thereby allowing material to enter (e.g., passively enter) the rectification section without a blower or compressor. A pump may be used to repressurize a return stream (e.g., $SS_{VS}$ and/or $RS_{LS}$) to allow it to return to the prefractionating column.

Fractionating a distillation feed may include heating and/or cooling one or more of the fractionation streams. According to some embodiments, fractionating a distillation feed may be performed within a temperature range of the column bottoms from about 10° C. to about 250° C., from about 120° C. to about 210° C., from about 120° C. to about 200° C., and/or from about 120° C. to about 175° C.

In some embodiments, the amount of material from a main section that moves back to a prefractionating section may be regulated. For example, a liquid internal stream (e.g., I2 and/or $RS_{LS}$) may return to a prefractionating section at a weight ratio ("liquid recycle ratio") of from about 0.01 to about 0.5 (e.g., from about 0.06 to about 0.133). For example, a vapor internal stream (e.g., 14 and/or SS$_{VS}$) may return to a prefractionating section at a weight ratio ("vapor recycle ratio") of from about 0 to about 0.75. The optimum values of the liquid recycle ratio and vapor recycle ratios may depend on the feed composition and may define the energy consumption required for the separation.

As will be understood by those skilled in the art who have the benefit of the instant disclosure, other equivalent or alternative compositions, devices, methods, and systems for fractionating a feed mixture (e.g., comprising one or more isocyanates) can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, a prefractionating apparatus may have a condenser in fluid communication with a rectification section, an intermediate reboiler in fluid communication with a prefractionating section and/or column, and a stripping section reboiler in fluid communication with a stripping section as described herein. A fractionating apparatus may or may not comprise, in some embodiments, any further condensers and/or reboilers. In addition, the size of a column (e.g., a dividing wall column) may be scaled up or down to suit the needs and/or desires of a practitioner. Also, where ranges have been provided, the disclosed endpoints may be treated as exact and/or approximations as desired or demanded by the particular embodiment. In addition, it may be desirable in some embodiments to mix and match range endpoints. A fractionation apparatus and/or system may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

EXAMPLES

Some specific example embodiments of the disclosure may be illustrated by one or more of the examples provided herein.

Example 1

Modeling Isocyanate Fractionation

An example of the present disclosure was modeled with ASPEN Plus™ software. The model included physical properties of the components validated against laboratory measurements, pilot data, and commercial data. Standard ASPEN Plus unit operation blocks were used to model the columns, reboilers, condensers, liquid and vapor splits. The efficiency of contact devices—contact trays and packing—was validated against the performance of commercial plant data.

The feed enters a prefractionating section of the column with 3 packed stages above and 5 stages below as trays. This prefractionating section separates ODCB from TDI and heavies before they enter the main column. This separation is driven by a reboiler in the prefractionating section. The pressure at the top of the prefractionating section is 50 mmHg. That pressure is higher than the pressure at which Stream I1 enters the main column (i.e., 33 mmHg). This pressure drop causes the vapor to flow without the need for an air blower or compressor. The liquid return to the top of the prefractionating section (Stream I2) has a pump to raise the pressure from 33 to 40 mmHg. At the bottom of the prefractionating section, the reboiler operates at 5270 kW and 171° C. The pressure drop across the prefractionating section is 25 mmHg (i.e., I3-I1).

As modeled, the main section of the column was much larger, with 23 stages of packing and 2 more stages with trays. The ODCB product is separated through a pasteurizer-like section of the rectification section, with the TDI product coming off as a side stream. A pasteurizer-like section may be used to withdraw distillate (upper product) a few trays (separation stages) below the top of the column. It may include a side draw used when a small amount of light component with a high relative volatility to the desired liquid overhead product can be taken out of the column with an acceptable loss of product. The two recycle streams, namely I2 and I4, are split off from the main column at different ratios. The liquid (stream I2) is split off at a ratio 0.06, i.e., only 6% of the liquid flows back to the first column. The vapor (stream I4) split is at 0.5.

These two split ratios may have an impact (e.g., a major impact) on column efficiency. An example of this impact is shown in Table 2. The rectification section condenser operates at 16100 kW and 61° C., at a pressure of 35 mmHg. The stripping section reboiler operates at 3490 kW and 196° C. with a pressure of 100 mmHg. These numbers result in a normalized stripping section reboiler duty of 0.33 kW-h/kg TDI. The normalized rectification section condenser duty is 0.61 kW-h/kg.

The material balance of the above example is shown in Table 2 below. FIG. 7 may be referenced for identification of the streams.

TABLE 2

| Stream | F1 | I1 | I2 | I3 | I4 | P2 | P3 | P4 |
|---|---|---|---|---|---|---|---|---|
| Temperature ° C. | 206 | 106 | 101 | 171 | 171 | 86 | 168 | 196 |
| Pressure mmHg | 1213 | 50 | 50 | 75 | 75 | 36 | 69 | 100 |
| Mass Flow kg/hr | 303205 | 268935 | 2707 | 68886 | 31909 | 253615 | 43838 | 5630 |
| Mass Fraction | | | | | | | | |
| Lights | 0.0001 | 0.0001 | 1 ppm | 0.0000 | 0.0000 | 7 ppm | 0.0000 | 0.0000 |
| Solvent | 0.8370 | 0.9502 | 0.6795 | 0.0001 | 0.0001 | 1.0000 | 48 ppm | 0.0000 |
| TDI | 0.1519 | 0.0496 | 0.3204 | 0.9520 | 0.9995 | 0.0000 | 0.9999 | 0.4141 |
| Heavies | 0.0109 | 1 ppm | 6 ppm | 0.0479 | 32 ppm | 0.0000 | 27 ppm | 0.58591 |

Example 2

Modeling Isocyanate Fractionation

An example of the present disclosure was modeled with ASPEN Plus software. The model included physical properties of the components validated against laboratory measurements, pilot data, and commercial data. Standard ASPEN Plus unit operation blocks were used to model the columns, reboilers, condensers, liquid and vapor splits. The efficiency of contact devices—contact trays and packing—was validated against the performance of commercial plant data.

The feed enters a first (prefractionating) column with 3 packed stages above and 5 stages below as trays. This first column separates ODCB from TDI and heavies before they enter the second (main) column. This separation is driven by a reboiler in the first column. The pressure at the top of the prefractionating section is 40 mmHg. That pressure is higher than the pressure at which Stream I1 enters the main column (i.e., 33 mmHg). This pressure drop causes the vapor to flow without the need for an air blower or compressor. The liquid return to the top of the first column (Stream I2) has a pump to raise the pressure from 33 to 40 mmHg. At the bottom of the first column, the reboiler operates at 5270 kW and 171° C. The pressure drop across the prefractionating column is 25 mmHg (i.e., I3-I1).

As modeled, the second (main) column was much larger, with 25 stages of packing and 2 more stages with trays. The ODCB product is separated through a pasteurizer-like section of the rectification section, with the TDI product coming off as a side stream. The two recycle streams, namely I2 and I4, are split off from the main column at different ratios. The liquid is split off at a ratio 0.06, i.e., only 6% of the liquid flows back to the first column. The vapor split is at 0.5. The vapor and liquid split may have major impact on the efficiency of a column. The numbers for the split in this example were obtained from case studies in order to minimize energy consumption in the apparatus. The rectification section condenser operates at 16100 kW and 61° C., at a pressure of 35 mmHg. The stripping section reboiler operates at 3490 kW and 196° C. with a pressure of 100 mmHg. These numbers result in a normalized stripping section reboiler duty of 0.33 kW-h/kg TDI. The normalized rectification section condenser duty is 0.61 kW-h/kg.

The material balance of the above example is shown in Table 2 above. FIG. 8 may be referenced for identification of the streams.

Example 3

Modeling Isocyanate Fractionation

An example of the present disclosure was modeled with ASPEN Plus software. The model included physical properties of the components validated against laboratory measurements, pilot data, and commercial data. Standard ASPEN Plus unit operation blocks were used to model the columns, reboilers, condensers, liquid and vapor splits. The efficiency of contact devices—contact trays and packing—was validated against the performance of commercial plant data.

The feed enters a first (prefractionating) column with 3 packed stages above and 5 stages below as trays. This first column separates ODCB from TDI and heavies before they enter the second (main) column. This separation is driven by a reboiler in the first column. The pressure at the top of the prefractionating section is 40 mmHg. That pressure is higher than the pressure at which Stream I1 enters the main column (i.e., 33 mmHg). This pressure drop causes the vapor to flow without the need for an air blower or compressor. The liquid return to the top of the first column (Stream I2) has a pump to raise the pressure from 33 to 40 mmHg. At the bottom of the first column, the reboiler operates at 6746 kW and 180° C. The pressure drop across the prefractionating column is 60 mmHg (i.e., I3-I1).

As modeled, the second (main) column was much larger, with 18 stages of packing and 2 more stages with trays. The ODCB product is separated through a pasteurizer-like section of the rectification section, with the TDI product coming off as a side stream. The liquid recycle stream, namely I2, is split off from the main column at a ratio 0.13, i.e., only 13% of the liquid flows back to the first column. The rectification section condenser operates at 16510 kW and 70° C., at a pressure of 30 mmHg. The stripping section reboiler operates at 2026 kW and 173° C. with a pressure of 30 mmHg. These numbers result in a normalized stripping section reboiler duty of 0.35 kW-h/kg TDI. The normalized rectification section condenser duty is 0.55 kW-h/kg.

The material balance of the above example, according to the simulation, is the same as shown for Example 2 in Table 2 above. This suggests that these systems may be thermodynamically equivalent and/or substantially equivalent under at least some conditions. FIG. 9 may be referenced for identification of the streams.

What is claimed is:

1. A method for fractionating an isocyanate feed mixture comprising a light component comprising lights and solvent, a middle-boiling component comprising an isocyanate, and a heavy boiling component comprising other components of the feed mixture heavier than light, solvent, and isocyanate, using a fractionating apparatus comprising a prefractionating section, a rectification section, a stripping section, and a side section, the method comprising:

(a) moving the isocyanate feed mixture after stripping in a stripping section into the prefractionating section, (b) warming the contents of the prefractionating section and forming a prefractionating section vapor stream $PS_{VS}$ and a prefractionating section liquid stream $PS_{LS}$ by heating at least a portion of the prefractionating section liquid stream $PS_{LS}$ in at least one external reboiler, (c) moving at least a portion of the prefractionating section vapor stream $PS_{VS}$ to the rectification section, (d) cooling the contents of the rectification section to form a rectification section vapor product stream $RS_{VPS}$ and a condensate liquid, (e) removing from the fractionating apparatus at least a portion of the rectification section vapor product stream $RS_{VPS}$, (f) removing from the fractionating apparatus at least a portion of the condensate liquid as a rectification section liquid product stream $RS_{LPS}$, (g) removing from the rectification section at least a portion of the condensate liquid as a rectification section liquid stream $RS_{LS}$, (h) moving at least a portion of the rectification section liquid stream $RS_{LS}$ to the side section, (i) moving at least a portion of the rectification section liquid stream $RS_{LS}$ to the prefractionating section, (j) heating at least a portion of the prefractionating section liquid stream $PS_{LS}$ to form a second prefractionating section vapor stream $sPS_{VS}$ and a second prefractionating section liquid stream $sPS_{LS}$ and combining each with their respective first streams, (k) moving at least a portion of the prefractionating section liquid stream $PS_{LS}$ from the prefractionating section to the stripping section, (l) heating the contents of the stripping section to form a stripping section vapor stream $SS_{VS}$ and a stripping section lower product stream $SS_{LPS}$, (m) removing from the fractionating apparatus at least a portion of the stripping section liquid product stream $SS_{LPS}$, (n) moving at least a portion of the stripping section vapor stream $SS_{VS}$ to the side section, (o) commingling at least a portion of the rectification section liquid stream $RS_{LS}$ and at least a portion of the stripping section vapor stream $SS_{VS}$ in the side section under conditions that permit formation of a side section vapor stream $SdS_{VS}$, a side section liquid product stream $SdS_{LPS}$, and a side section liquid stream $SdS_{LS}$, (p) removing from the fractionating apparatus at least a portion of the side section liquid product stream $SdS_{LPS}$, (q) moving at least a portion of the side section vapor stream $SdS_{VS}$ to the rectification section, and (r) moving at least a portion of the side section liquid stream $SdS_{LS}$ to the stripping section, wherein the concentration of the light component in the isocyanate feed mixture is from about 5 weight percent or molar percent to about 90 weight percent or molar percent, the concentration of the middle-boiling component in the isocyanate-containing feed mixture is from about 2 weight percent or molar percent to about 95 weight percent or molar percent, and the concentration of the heavy boiling component in the isocyanate-containing feed mixture is from about 0.1 weight percent or molar percent to about 50 weight percent or molar percent, with the proviso that the concentration of the light component is (i) higher than the middle-boiling component and (ii) higher than the heavy boiling component.

2. A method for fractionating an isocyanate feed mixture according to claim 1, wherein the middle-boiling component comprises less than about 20 weight percent of the isocyanate feed mixture.

3. A method for fractionating an isocyanate feed mixture according to claim 1, wherein the weight or molar ratio of the side section liquid product stream $SdS_{LPS}$ to the isocyanate feed mixture is more than about 20%.

4. A method for fractionating an isocyanate feed mixture according to claim 1, wherein the side section liquid product stream $SdS_{LPS}$ comprises an isocyanate.

5. A method for fractionating an isocyanate feed mixture according to claim 1, wherein the side section liquid product stream $SdS_{LPS}$ comprises toluene diisocyanate.

6. A method for fractionating an isocyanate feed mixture according to claim 1, wherein the side section liquid product stream $SdS_{LPS}$ consists of one or more isocyanates.

7. A method for fractionating an isocyanate feed mixture according to claim 1, wherein (j) heating at least a portion of the prefractionating section liquid stream $PS_{LS}$ to form a second prefractionating section vapor stream $sPS_{VS}$ and a second prefractionating section liquid stream $sPS_{LS}$ comprises heating at least a portion of the prefractionating section liquid stream $PS_{LS}$ in at least one internal reboiler or in at least one external reboiler.

8. A method for fractionating an isocyanate feed mixture according to claim 1, wherein the prefractionating section, the rectification section, the stripping section, and the side section form a non-adiabatic dividing wall column.

9. A method for fractionating an isocyanate feed mixture according to claim 1, wherein (i) moving at least a portion of the rectification section liquid stream $RS_{LS}$ to the prefractionating section further comprises:

moving the at least a portion of the rectification section liquid stream $RS_{LS}$ to the prefractionating section, wherein the weight or molar ratio of the at least a portion of the rectification section liquid stream $RS_{LS}$ to the prefractionating section vapor stream $PS_{VS}$ is from about 0 to about 0.75.

10. A method for fractionating an isocyanate feed mixture according to claim 1 further comprising (s) moving at least a portion of the stripping section vapor stream to the prefractionating section.

11. A method for fractionating an isocyanate feed mixture according to claim 10, wherein (s) moving at least a portion of the stripping section vapor stream $SS_{VS}$ to the prefractionating column further comprises:

moving the at least a portion of the stripping section vapor stream $SS_{VS}$ to the prefractionating section, wherein the weight or molar ratio of the at least a portion of the stripping section vapor stream $SS_{VS}$ to the prefractionating section liquid stream $PS_{LS}$ is from about 0.01 to about 0.5.

12. A method for fractionating an isocyanate feed mixture according to claim 1 further comprising maintaining a pressure in the prefractionating section that is higher than the pressure in the rectification section.

13. A method for fractionating an isocyanate feed mixture according to claim 1 further comprising maintaining a pressure in the fractionating apparatus that is less than atmospheric pressure.

14. A method for fractionating an isocyanate feed mixture according to claim 1 further comprising maintaining at least a portion of the fractionating apparatus at a temperature of from about 50° C. to about 250° C.

15. A method for fractionating an isocyanate feed mixture according to claim 8, wherein the non-adiabatic fractionating apparatus consumes from about 0.4 to about 1.0 kilowatts per kilogram of isocyanate produced in the side section liquid product stream $SdS_{LPS}$.

16. A method for fractionating an isocyanate feed mixture according to claim 8, wherein the non-adiabatic fractionating apparatus consumes less than about 0.4 kilowatts per kilogram of isocyanate produced in the side section liquid product stream $SdS_{LPS}$.

* * * * *